(12) United States Patent
Jensen et al.

(10) Patent No.: US 12,203,137 B2
(45) Date of Patent: Jan. 21, 2025

(54) USE OF ADIPOQ GENE EXPRESSION LEVEL FOR CLASSIFICATION OF A SUBJECT IN RISK GROUPS IN THE PROGNOSIS OR DIAGNOSIS OF TYPE II DIABETES MELLITUS

(71) Applicant: Lipozyt Marker UG, Bremen (DE)

(72) Inventors: Uwe Jensen, Bremen (DE); Wolfgang Hierneis, Hamburg (DE); Markus Klemke, Bremen (DE); Helge Wilhelm Thies, Bremen (DE)

(73) Assignee: LIPOZYT MARKER UG, Bremen (DE)

( * ) Notice: Subject to any disclaimer, the term of this patent is extended or adjusted under 35 U.S.C. 154(b) by 596 days.

(21) Appl. No.: 16/766,366

(22) PCT Filed: Nov. 19, 2018

(86) PCT No.: PCT/EP2018/081681
§ 371 (c)(1),
(2) Date: Jun. 26, 2020

(87) PCT Pub. No.: WO2019/101663
PCT Pub. Date: May 31, 2019

(65) Prior Publication Data
US 2020/0377948 A1   Dec. 3, 2020

(30) Foreign Application Priority Data

Nov. 24, 2017 (DE) .......................... 102017127857.5

(51) Int. Cl.
*C12Q 1/6883* (2018.01)
(52) U.S. Cl.
CPC ...... *C12Q 1/6883* (2013.01); *C12Q 2600/118* (2013.01); *C12Q 2600/158* (2013.01)
(58) Field of Classification Search
CPC ............ C12Q 1/6883; C12Q 2600/112; C12Q 2600/118; C12Q 2600/158
See application file for complete search history.

(56) References Cited

FOREIGN PATENT DOCUMENTS

| DE | 102015208083 | * 10/2016 |
|----|--------------|-----------|
| WO | WO 2016/131943 | * 8/2016 |
| WO | 2017021815 | 2/2017 |

OTHER PUBLICATIONS

Lihn, Aina S., et al. "Adiponectin expression in adipose tissue is reduced in first-degree relatives of type 2 diabetic patients." American journal of physiology-endocrinology and metabolism 284.2 (2003): E443-E448. (Year: 2003).*

J. Perren Cobb, et al. "Sepsis gene expression profiling: Murine splenic compared with hepatic responses determined by using complementary DNA microarrays" Crit Care Med 2002 vol. 30, No. 12. (Year: 2002).*
Y. Hoshikawa, et al. "Hypoxia induces different genes in the lungs of rats compared with mice" Physiol Genomics 12: 209-219, 2003. (Year: 2003).*
Philip A. Kern, et al. "Adiponectin Expression From Human Adipose Tissue—Relation to Obesity, Insulin Resistance, and Tumor Necrosis Factor-a Expression" Diabetes, vol. 52, Jul. 2003 (Year: 2003).*
Vivian G. Cheung, et al., "Natural variation in human gene expression assessed in lymphoblastoid cells" Nature Genetics, vol. 33, Mar. 2003 (Year: 2003).*
Guoan Chen, et al. "Discordant Protein and mRNA Expression in Lung Adenocarcinomas"Molecular & Cellular Proteomics 1.4 (Year: 2002).*
G. Atzmon, et al. "Differential gene expression between visceral and subcutaneous fat depots" Horm Metab Res (2002) 34: 622-628. (Year: 2002).*
Owei et al., "Insulin-sensitive and insulin-resistant obese and non-obese phenotypes: role in prediction of incident pre-diabetes in a longitudinal biracial cohort", BMG Open Diabetes Research & Care, vol. 5, No. 1, Jul. 2017, pp. 1-9.
Yaghootar et al., "Genetic Evidence for a Normal-Weight 'Metabolically Obese' Phenotype Linking Insulin Resistance, Hypertension, Coronary Artery Disease, and Type 2 Diabetes", Diabetes, vol. 63, Dec. 2014, pp. 4369-4377.
Xi et al., "HMGA2 promotes adipogenesis by activating C/EBP[beta]-mediated expression of PPAR [gamma]", Biochemical and Biophysical Research Communications, vol. 472, Apr. 2016, pp. 618-623.
Westerlund, "Classication with Kohonen Self-Organizing Maps", Soft Computing, Haskoli Islands, Apr. 24, 2005, pp. 1-16.
Tenorio et al., "Visceral Adiposity Measurements, Metabolic and Inflammatory Profi le in Obese Patients with and Without Type 2 Diabetes Mellitus: A Crosssectional Analysis", Current Diabetes Reviews, Bentham Science Publishers LTD, vol. 13, Jan. 2017, pp. 11-18.
Li et al., "Identification of type 2 diabetes subgroups through topological analysis of patient similarity", Science Translational Medicine, Oct. 2015, vol. 28, No. 7, pp. 1-31.
Gastaldelli et al., "Role of Adipose Tissue Insulin Resistance in the Natural History of Type 2 Diabetes: Results From the San Antonio Metabolism Study", Diabetes, vol. 66, Apr. 2017, pp. 815-822.
Yao et al., "Association of ADIPOQ variants with type 2 diabetes mellitus susceptibility in ethnic Han Chinese from northeast China", Journal of Diabetes Investigation, vol. 7, 2016, pp. 853-859.

(Continued)

*Primary Examiner* — Amanda Haney
(74) *Attorney, Agent, or Firm* — DUANE MORRIS LLP; Gregory M. Lefkowitz; Brandon A. Chan

(57) ABSTRACT

The invention is directed to using of the relative value of the gene expression level of the gene for ADIPOQ and/or of a gene, the expression of which has linear statistical correlation with that of the ADIPOQ gene, in the prognosis or the diagnosis of a type II diabetes mellitus disease in a test subject. Also disclosed is a method for prognosing and/or diagnosing a type II diabetes mellitus disease for classification of a subject into risk groups, wherein the gene expression level of the ADIPOQ gene and/or of a gene, the expression of which has linear statistical correlation with that of the ADIPOQ gene, is determined and the subject is subsequently classified into risk groups, taking said gene expression level into account.

8 Claims, 17 Drawing Sheets

(56) References Cited

OTHER PUBLICATIONS

Figure 1:
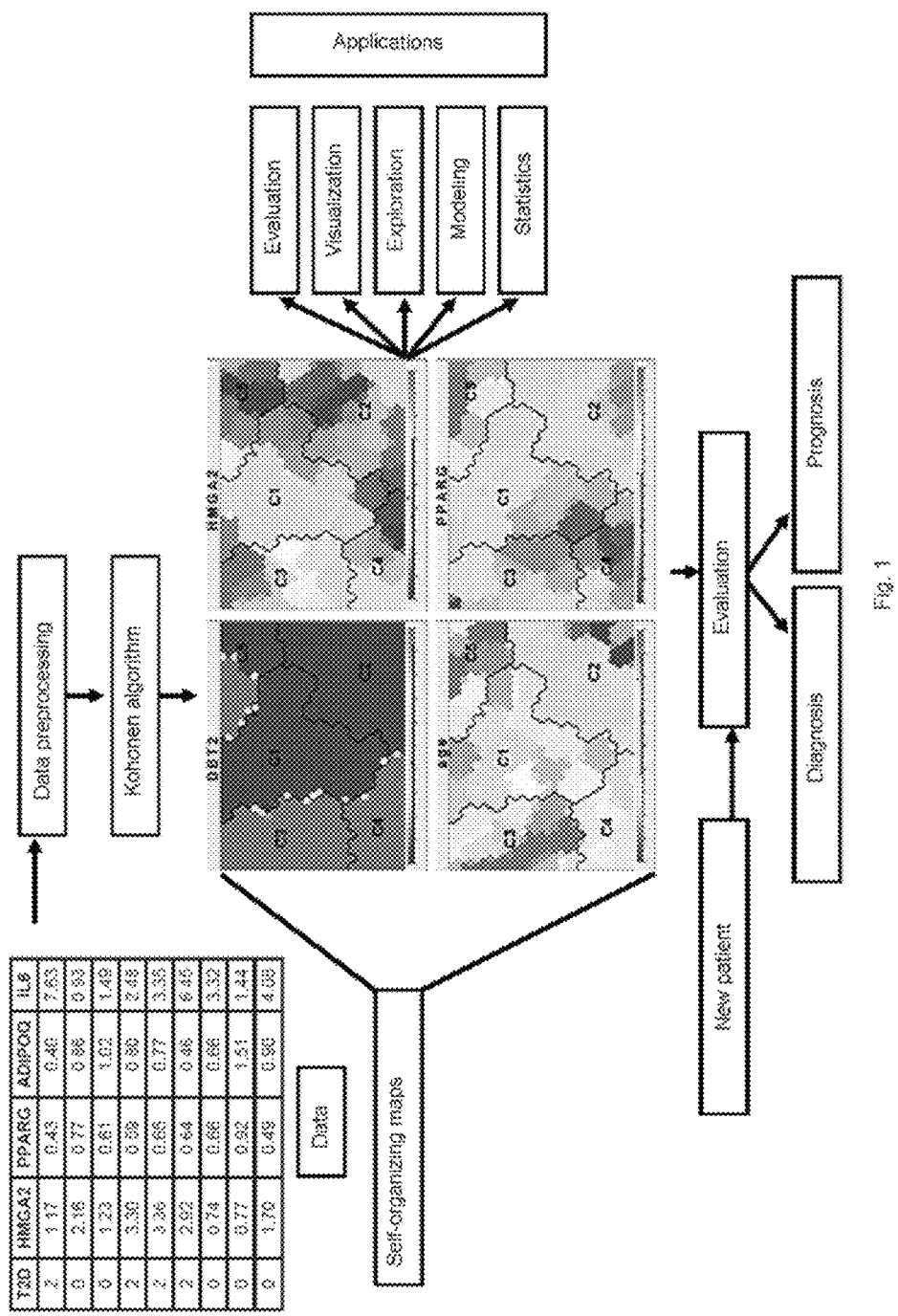

Aleidi et al., "Adiponectin serum levels correlate with insulin resistance in type 2 diabetic patients", King Saud University, Saudi Pharmaceutical Journal, vol. 23, 2015, pp. 250-256.

Tomiyama et al., "Misclassification of cardiometabolic health when using body mass index categories in NHANES", 2016, Int J Obes (Lond), pp. 1-4.

Szmitko et al., "Adiponectin and cardiovascular disease: state of the art?", 2007, Am J Physiol Heart Circ Physiol. vol. 292, pp. H1655-63.

Blog post, www.visualcinnamon.com/2013/07/self-organizing-maps-creating-hexagonal.html, 10 pages.

Quinlan, "Induction of decision trees. In: Machine Learning", 1986, vol. 1, pp. 81-106.

Quinlan, "Improved use of continuous attributes in C4.5", 1996, Journal of artificial intelligence research 4, pp. 77-90.

Schwarz, "Estimating the dimension of a model", 1978, Annals of Statistics, vol. 6, No. 2, pp. 461-464.

* cited by examiner

USE OF ADIPOQ GENE EXPRESSION LEVEL FOR CLASSIFICATION OF A SUBJECT IN RISK GROUPS IN THE PROGNOSIS OR DIAGNOSIS OF TYPE II DIABETES MELLITUS

CROSS-REFERENCE TO RELATED APPLICATIONS

This application is a § 371 national stage entry of International Application No. PCT/EP2018/081681, filed on Nov. 19, 2018, which claims priority to German Patent Application No. 102017127857.5, filed on Nov. 24, 2017, the entire contents of which are incorporated herein by reference.

The invention relates to the use of the relative value of the gene expression level of the gene for ADIPOQ and/or of a gene, the expression of which has linear statistical correlation with that of the ADIPOQ gene, in the prognosis or the diagnosis of a type II diabetes mellitus disease in a test subject. It further relates to a method for prognosing and/or diagnosing a type II diabetes mellitus disease for classification of a subject into risk groups, wherein the gene expression level of the ADIPOQ gene and/or of a gene, the expression of which has linear statistical correlation with that of the ADIPOQ gene, is determined and the subject is subsequently classified into risk groups, taking said gene expression level into account.

The prevalence of overweight and obesity and also diseases associated therewith, such as type II diabetes mellitus (T2D), is a problem which is advancing globally. According to the World Health Organization (WHO), overweight is defined from a body mass index (BMI) of ≥25 kg/m²-<30 kg/m² and obesity is defined from a BMI of ≥30 kg/m². Obesity is divided into further grades: obesity grade I (BMI=30-34.9 kg/m²), obesity grade II (BMI=35-39.9 kg/m²), obesity grade III (BMI≥40 kg/m²) and super-obesity (BMI≥50 kg/m²). Developing T2D is not necessarily always a result of a high BMI; on the contrary, the BMI can only serve as a very rough predictor. Even normal-weight people (BMI<25 kg/m²) develop T2D, and the exact scientific background as to why normal-weight people also develop diseases that are more associated with overweight and obesity are still unclear.

Tomiyama et. al. (Tomiyama A J, Hunger J M, Nguyen-Cuu J, Wells C (2016) Misclassification of cardiometabolic health when using body mass index categories in NHANES 2005-2012. Int J Obes (Lond) 40: 883-6) showed, on the basis of measured blood parameters in a study with 40 420 participants, that 50% of the overweight individuals examined therein and 29% of individuals suffering from obesity were considered cardiometabolically healthy, which could not be expected from a classification based only on the BMI. Moreover, 30% of the normal-weight individuals examined therein had an unhealthy cardiometabolic state. However, the measured blood parameters only show the current state of the subjects and only reflect a brief, past period of cardiometabolic maldevelopment in the subjects. The HbA1c assay, for example, provides information about the blood glucose level of the last 4-12 weeks and a person is considered diabetic from an HbA1c value of ≥6.5%.

A T2D disease is characterized by a relative insulin deficiency and/or an insulin resistance of the tissues in the body. During the pathogenesis of T2D, insulin resistance and production increases more and more over many years up to a point at which the insulin-producing β cells of the pancreas become dysfunctional owing to the years of overuse and reduce insulin production. This point in time is considered to be the start of a T2D disease, but it likewise takes again several years on average until the diabetic is recognized as a diabetic by the physician (Pearson J, Powers M A (2006) Systematically initiating insulin: the staged diabetes management approach. Diabetes Educ 32 (Suppl): 19S-28S). In contrast to type 1 diabetes (T1D), where the cause of the diabetes is a dysfunctional pancreas, what may be the cause of T2D pathogenesis in T2D is not only the pancreas, but also the liver, muscles and/or maldevelopments in adipose tissue. Just by determining the HbA1c value, it is not yet possible to achieve a relatively specific diagnosis and resultant personalized treatment of T2D diabetics. Personalized treatment can only be achieved by subdivision of the T2D disease into subclasses. To date, there is no reliable diagnostic method that allows subclassification of diabetics. Thus, there is a need for differentiated methods, both in the prognosis and in the diagnosis of diabetics.

Against this background, it is an object of the present invention to specify a new possibility which allows a prognosis and/or diagnosis that is different or additionally differentiated in relation to the prior art.

According to the invention, this object is achieved by use of the relative value of the gene expression level of the gene for ADIPOQ and/or of a gene, the expression of which has linear statistical correlation with that of the ADIPOQ gene, such as in particular PRAR gamma, in the prognosis and/or the diagnosis of a type II diabetes mellitus disease in a subject, the subject being classified into one of at least three risk groups, at least two of the possible risk groups consisting of individuals who have already formed type II diabetes mellitus.

One possibility of making an early diagnosis of a maldevelopment with respect to insulin resistance and insulin production lies in, inter alia, adipose tissue, which can, as a long-term store for fats and glucose, cushion malnutrition over a very long period. A dysfunctional adipose tissue is presumably a critical element for the genesis of T2D, both in overweight/obese individuals and in individuals of normal weight. Various study results show that adipose tissue is increasingly considered to be an endocrine organ which actively intervenes in or controls physiological processes. The substances secreted by adipose tissue, which are called adipokines, are, inter alia, associated with insulin sensitivity and resistance, reproduction, inflammation and bone growth and with immunological processes and fatty acid metabolism. One adipokine associated with the predisposition for the development of T2D is adiponectin (Szmitko P E, Teoh H, Stewart D J, Verma S (2007) Adiponectin and cardiovascular disease: state of the art? At the J Physiol Heart Circ Physiol. 292: H1655-63).

Human adiponectin is encoded by the APM1/ACDC/ACRP30/GBP28/ADIPOQ gene (accession ID: D45371), which is located in chromosome band 3q27. It contains three exons which lie in a 17 kb region. Exons one and two are respectively 76 bp and 222 bp in size and are separated by intron one, which is 10.3 kb in size. Exon three comprises approximately 4.28 kb. Translation starts in exon two and ends in exon three and thus leaves exon one and parts of exon three untranslated. The 30 kDa adiponectin protein is mainly produced and secreted by adipocytes. Adiponectin consists of a carboxy-terminal globular domain and a collagen domain in the amino-terminal end. In blood plasma, adiponectin occurs as a complete protein of 244 amino acids in length and as a proteolytic cleavage-product fragment, also called globular adiponectin. Isoforms of adiponectin arise owing to different linkages between the globular and collagen domains. The action of adiponectin on the cells of the body is mediated via the AdipoR1 and AdipoR2 receptors. AdipoR1 and AdipoR2 are primarily to be found in skeletal muscle and in liver cells, respectively. However, further studies indicate that AdipoR1 and AdipoR2 are also expressed in cardiomyocytes, osteoblasts and β cells of the pancreas. Adiponectin plays an eminent role in lipid and glucose metabolism. It brings about a change in insulin sensitivity via activation of 5' adenosine monophosphate-activated protein kinase (AMPK) and improves insulin resistance by increasing fatty acid oxidation and suppressing gluconeogenesis in the liver. Besides the increased risk of diabetes and a diabetic angiopathy, a deficiency of adiponectin is also associated with an increased risk of heart attacks and strokes.

"Adiponectin" in the context of this text is accordingly the adiponectin protein or the gene thereof or the associated mRNA and/or parts of this protein or gene (or the mRNA thereof), preferably at least one amino acid chain ≥7 amino acids, further preferably ≥15 amino acids and particularly preferably ≥20 amino acids or a nucleic acid chain of ≥20 nucleic acids, further preferably ≥40 nucleic acids and particularly preferably ≥55 nucleic acids, per strand where applicable. Adiponectin is an important adipokine that is involved in the control of fat metabolism and insulin sensitivity and has a direct antidiabetic, antiatherogenic and anti-inflammatory influence. It stimulates AMPK phosphorylation and activation in the liver and skeletal muscle, with a resultant increase in the utilization of glucose and in the burning of fatty acids. The human adiponectin gene is located in chromosome region 3q27 and consists of three exons, which extend over a region ≥17 kb in length. It encodes, inter alia, a complete adiponectin protein of 244 amino acids in length, the molecular mass of which is 30 kDa. The adiponectin protein is characterized by a carboxy-terminal globular domain and a collagen domain in the amino-terminal end. Adiponectin basically occurs in plasma as a complete protein (244 amino acids) and as a proteolytic cleavage-product fragment, also called globular adiponectin. The isoforms of adiponectin arise owing to different linkages between the globular and collagen domains. Three main complexes in particular circulate in plasma, a low-molecular-weight trimer (LMW), a medium-molecular-weight hexamer (MMW) and a high-molecular weight complex (HMW).

The value for the relative gene expression level in the context of the present invention can be achieved in any manner known to a person skilled in the art. Preference is given to determining the gene expression level at the mRNA level or at the protein level. In this connection, the mRNA level is preferred.

In the present invention, relative gene expression levels are determined. Where mention is merely made of "gene expression levels" hereinafter, relative gene expression levels is always meant, unless otherwise noted. In this connection, the relative gene expression levels are preferably determined by determination of the gene expression level of the gene to be studied in relation to the expression level of a housekeeping gene, preferably selected from the group consisting of HPRT, 18S rRNA, GAPDH, GUSB, PBGD, B2M, ABL, RPLP0, very particular preference being given to HPRT.

In the context of this text, the term "prognosis" means a prediction an increased probability of the development or the occurrence of a clinical state or a disease.

In the context of this text, the term "diagnosis" of a disease means that a disease already showing clinical symptoms is identified and/or confirmed.

Type II diabetes mellitus is also abbreviated to T2D hereinafter in the text.

"Subject" in the context of the present application are people and animals, the preferred meaning being people.

"Risk groups" in the context of this text are those groups which can be separated from one another through suitable distinguishing features and have in each case a common increased or nonincreased risk with regard to the development or the presence of a disease, especially T2D. Moreover, risk groups can be additionally distinguished from one another by further physiological differences, and this may have therapeutic or prophylactic relevance.

It has emerged that, on the basis of the use according to the invention, it is surprisingly possible to make a further differentiation within the group of individuals suffering from type II diabetes mellitus (subjects). This differentiation is helpful when finding suitable therapies for the particular individual.

For example, such a therapeutic approach could be that drugs which influence the adiponection level are given depending on the expression of ADIPOQ within the T2D sufferers. For example, it might be possible to raise the adiponectin level in the groups of relatively low ADIPOQ expression. A suitable drug therefor might be metformin.

Part of the invention is also a method for prognosing and/or diagnosing a type II diabetes mellitus disease, comprising the steps of:
 a) providing a sample from a subject,
 b) determining the gene expression level of the ADIPOQ gene and/or of a gene, the expression of which has linear/statistical correlation with that of the ADIPOQ gene, in the sample and
 c) classifying the subject into one of at least three risk groups, taking the gene expression levels of the ADIPOQ gene and/or of a gene, the expression of which has linear statistical correlation with that of the ADIPOQ gene, into account, at least two of the possible risk groups consisting of individuals who have already formed type II diabetes mellitus.

As already described for the use according to the invention, the surprising result of the involvement of the relative gene expression level of the ADIPOQ gene and/or of a gene, the expression of which has statistical correlation with that of the ADIPOQ gene, in one of at least three risk groups is the possibility of establishing within the subjects already suffering from type II diabetes mellitus a further differentiation which can, in turn, be used for therapeutic purposes.

In the present invention, it is preferred according to the invention that the gene expression level of a gene selected from the group consisting of HMGA2 and IL-6 is further taken into account in the classification of the subjects in step c).

"HMGA2" in the context of this text is high mobility group AT-hook protein 2 (HMGA2) or the gene thereof or the associated mRNA and/or parts of this protein or gene (or the mRNA thereof), preferably at least one amino acid chain ≥7 amino acids, further preferably ≥15 amino acids and particularly preferably ≥20 amino acids or a nucleic acid chain of ≥20 nucleic acids, further preferably ≥40 nucleic acids and particularly preferably ≥55 nucleic acids, per strand where applicable. HMGA2 is a transcription factor which influences the regulation of gene expression and belongs to the group of high mobility group A proteins (HMGA proteins). The HMGA proteins are chromatin-associated, acid-soluble nonhistone proteins which bind to sequence-independent, specific motifs of DNA. As architectural transcription factors, they increase or inhibit, via structural changes in chromatin organization, the ability to bind further transcription factors. The human HMGA2 gene is located in chromosome region 12q14~15 and consists of five exons, which extend over a ≥160 kb region. It encodes a protein of 109 amino acids in length, the molecular mass of which is 12 kDa. The HMGA2 protein is characterized by three highly conserved DNA-binding domains, the so-called AT hooks and an acidic negatively charged C-terminal domain.

"PPAR gamma" in the context of this text is peroxisome proliferator-activated receptor gamma (PPAR gamma) or the gene thereof or the associated mRNA and/or parts of this protein or gene (or the mRNA thereof) preferably at least one amino acid chain ≥7 amino acids, further preferably ≥15 amino acids and particularly preferably ≥20 amino acids or a nucleic acid chain of ≥20 nucleic acids, further preferably ≥40 nucleic acids and particularly preferably ≥55 nucleic acids, per strand where applicable. PPAR gamma is a ligand-binding nuclear transcription factor of the PPAR subfamily, which belongs to the group of nuclear hormone receptors. PPAR gamma activates the transcription of various genes via heterodimerization with retinoid X receptor α (RXRα). The human PPAR gamma gene is located in chromosome band 3p25 and consists of 11 exons. The human PPAR gamma gene encodes 2 isoforms, which are a protein of 477 amino acids in length and a protein of 505 amino acids in length.

"IL-6" in the context of this text is interleukin-6 or the gene thereof or the associated mRNA and/or parts of this protein or gene (or the mRNA thereof), preferably at least one amino acid chain ≥7 amino acids, further preferably ≥15 amino acids and particularly preferably ≥20 amino acids or a nucleic acid chain of ≥20 nucleic acids, further preferably ≥40 nucleic acids and particularly preferably ≥55 nucleic acids, per strand where applicable. Interleukin-6 is a cytokine which plays a role both in inflammatory reactions and in the maturation of B lymphocytes. Furthermore, it has been demonstrated that the substance is an endogenous substance with inflammatory action, a so-called pyrogen, that can trigger a high fever in the event of autoimmune diseases or infections. The protein is predominantly generated at sites of acute or chronic inflammation, from where it is secreted into serum and triggers an inflammatory reaction via the interleukin-6 receptor alpha. Interleukin-6 is involved in various disease states associated with inflammation, including a predisposition for diabetes mellitus or systemic juvenile idiopathic arthritis (Still's disease). The human IL-6 gene is located in chromosome band 7p15.3 and consists of six exons. The IL-6 precursor protein consists of 212 amino acids. After a signal peptide of 28 amino acids in length has been cleaved off, the mature interleukin-6 has a length of 184 amino acids (Hirano T, Yasukawa K, Harada H, Taga T, Watanabe Y, Matsuda T, Kashiwamura S, Nakajima K, Koyama K, Iwamatsu A, et al., 1986. Complementary DNA for a novel human interleukin (BSF-2) that induces B lymphocytes to produce immunoglobulin. Nature 324: 73-76).

It has emerged, then, that combining the data for ADIPOQ with those for the stated preferred genes leads to particularly reliable differentiation of groups within the risk groups in the use according to the invention or in the method according to the invention.

Preference is given to a method according to the invention or use according to the invention, wherein one or more features of the subject selected from the group consisting of age, BMI, height, weight, sex, abdominal and hip circumference, body fat percentage, muscle mass, total body water (TBW), blood pressure, smoker status, high blood pressure and ingestion of antihypertensive drugs are further taken into account for the classification into risk groups (in step c)).

By taking further features of the subjects into account, it is thus possible to produce an additional level of reliability of the subdivision within the risk groups. In some cases, it is self-evidently also possible to yet further refine the subdivision of the risk groups with each additional marker (taking a further feature into account).

In this sense, it is preferred according to the invention that one or more blood values of the subject selected from the group consisting of total cholesterol, triglycerides, HbA1c, HDL cholesterol, non-HDL cholesterol, LDL cholesterol, CRP, blood sugar, fasting blood sugar and preprandial blood sugar, postprandial blood sugar are further taken into account in the classification into the risk groups, especially in step c).

It is known that relevant statements about T2D status can be made by means of the blood values.

Further group differentiations can be produced with the aid of the use of ADIPOQ according to the invention in combination with the additional markers/blood parameters.

The following table points out typical values for blood parameters with a standard reference range according to "Leitlinie der Deutschen Diabetes Gesellschaft" [Guidelines of the German diabetes society] from 2012 and to the ESC/EAS Guidelines for the Management of Dyslipidaemias from 2016:

TABLE 1

| Parameter | Standard reference range (mg/dL) | In T2D group | In non-T2D group |
|---|---|---|---|
| Triglycerides | <150 | Increased | Not increased/low |
| Cholesterol, total* | <20 years: <170 | Increased | Not increased/low |
| | 20-30 years: <200 | | |
| | 30-40 years: <220 | | |
| | >40 years: <240 | | |
| HDL cholesterol | Men >40 | Lowered | Increased |
| | Women >48 | | |
| Non-HDL cholesterol + | Very high risk: <100 | Increased | Not increased/low |
| | High risk: <130 | | |
| | Low to moderate risk: <145 | | |

TABLE 1-continued

| Parameter | Standard reference range (mg/dL) | In T2D group | In non-T2D group |
|---|---|---|---|
| LDL cholesterol + | Very high risk: <70<br>High risk: <100<br>Low to moderate risk: <115 | Increased | Not increased/low |
| CRP | <5.0 mg/L | Increased | Not increased/low |
| Fasting glucose (venous plasma) | <100 | Increased | Not increased/low |
| 2 h glucose value (venous plasma) | <120 | Increased | Not increased/low |
| Preprandial glucose (venous plasma) | <100 | Increased | Not increased/low |
| HbA1c | <5.7% | Increased | Not increased/low |

*The average total cholesterol level of the 35- to 65-year-old age group in Germany is about 236 mg/dl, and the standard deviation is ± 46 mg/dl.
+ The grading is based on a very high risk, high risk and low to moderate risk for cardiovascular diseases (see the current guidelines from the European Society of Cardiology (ESC) and European Atherosclerosis Society (EAS) for 2016: ESC / EAS Guidelines for the Management of Dyslipidaemias). The risk can be calculated by means of a SCORE (Systematic Coronary Risk Estimation). The most common score systems are the ESC SCORE and the PROCAM SCORE (Prospective Cardiovascular Munster Study).

Here, according to the invention, in the differentiation of the status of the respective blood values, a good combination with other markers can lead to additional subdivision within the risk groups upon suitable evaluation (cf. also below).

Preference is given to a method according to the invention, wherein the sample was obtained from adipose tissue.

In this connection, the "sample from adipose tissue" is to be understood to mean that sample which provides the values for at least one gene expression level, preferably for all gene expression levels, that are used for step c). Self-evidently, the blood values cannot be obtained from adipose tissue.

For the preferred method according to the invention, it is preferred that the sample from adipose tissue was obtained by puncture of subcutaneous abdominal adipose tissue.

By means of fan-shaped punctures under suction, it is possible to obtain particularly good cells and cell clusters which allow molecular genetics analysis. Firstly, the fan-shaped puncture procedure reduces clogging/blockage of the cannula tip with adipose cells and, secondly, cells from various regions of the adipose tissue in question are obtained and a representative cross-section of the distribution of different cell types of adipose tissue is thus had.

Particular preference is given to a method according to the invention, wherein the sample mass for the samples from adipose tissue is ≤50 mg, preferably ≤20 mg and further preferably ≤5 mg.

It became apparent that, surprisingly, differentiated results can be reliably achieved even with very small sample volumes from adipose tissue. In this connection, it is particularly preferred that the sample was obtained by puncture as fine-needle aspirate.

In the view of the inventors, the determination of the various parameters from adipose tissue also has the following advantages in the prognostic sense: Firstly, according to the invention, it is possible, after the determination of the parameters from adipose tissue, to identify different risk groups of individuals who are already suffering from type II diabetes mellitus without, for example, the need for further determinations of blood samples. Secondly, the determination of the parameters from adipose tissue that is according to the invention allows earlier identification of individuals who have an increased probability of forming type II diabetes mellitus than in the case of, for example, conventional HbA1c assays. Said HbA1c assays only report information about the blood sugar level of the last four to 12 weeks and are thus rather less suitable for a longer-term prognosis in relation to forming type II diabetes mellitus.

Preferably according to the invention, the subject is a person, since a differentiated prognosis and diagnosis in the case of T2D in people is of very particular importance both in relation to the economy and in relation to health policy.

As already indicated above, it is preferred that the determination of the gene expression level is done at the mRNA level. Thus, it is possible to obtain reliable data using extremely low sample amounts and by means of established methods.

Preference is given to a method according to the invention, wherein the classification into the risk groups (in step c)) is done using the multivariate model of self-organizing maps by Kohonen.

In relation to the methodology of self-organizing maps, reference is made to the methods section below.

Preference according to the invention is given to a method or use, wherein the classification in step c) is done into one of at least 5 groups, at least two of the groups consisting of individuals who have an increased probability of forming type II diabetes mellitus.

Specifically, it has emerged that, by taking the relative gene expression level of ADIPOQ or genes having linear statistical correlation therewith into account, it is possible to also make a differentiation within the groups of individuals/subjects who have an increased probability of forming type II diabetes mellitus. From this knowledge as well, it is possible to derive therapeutic approaches or suitable preventive measures.

Further preference is given to a method according to the invention, wherein the gene expression level is measured at the mRNA level relative to the gene expression level of a housekeeping gene. This methodology is particularly suitable for obtaining reliable results from low sample amounts.

Preference is given to a method according to the invention, wherein the groups with the marker situation I) lowered relative gene expression level for ADIPOQ, greatly increased relative gene expression level for HMGA2 and also at least one of the marker situations selected from the group consisting of increased HbA1c blood values, increased cholesterol values, increased triglycerides, lowered HDL cholesterol, increased non-HDL cholesterol, increased LDL cholesterol, increased CRP, increased blood sugar, increased fasting blood sugar, increased preprandial blood sugar, increased postprandial blood sugar and age ≥45, and II) lowered relative gene expression level for ADIPOQ, lowered relative gene expression level for HMGA2 and also at least one of the marker situations selected from the group consisting of increased HbA1c blood values, increased cholesterol values, increased triglycerides, lowered HDL cholesterol, increased non-HDL cholesterol, increased LDL cholesterol, increased CRP, increased blood sugar, increased fasting blood sugar, increased preprandial blood sugar, increased postprandial blood sugar and age ≥45 are available as possible groups for a classification in step c).

These two preferred available classification possibilities express the additional potential of the use of the data from ADIPOQ in a particular form. With the respective combinations of marker values (the combination of always three values), it is possible—besides the classification possibilities into further groups—to use the classification possibilities preferred according to the invention. As a result, it is possible to obtain a reliable additional statement of a distinguishability of the subjects/individuals suffering from T2D.

Preference is given to a method according to the invention, wherein the groups with the marker situation
- III) greatly increased relative gene expression level for ADIPOQ, lowered relative gene expression level for HMGA2 and also at least one of the marker situations selected from the group consisting of increased HbA1c blood values, increased cholesterol values, increased triglycerides, lowered HDL cholesterol, increased non-HDL cholesterol, increased LDL cholesterol, increased CRP, increased blood sugar, increased fasting blood sugar, increased preprandial blood sugar, increased postprandial blood sugar and age ≥45,
- IV) increased relative gene expression level for ADIPOQ, lowered relative gene expression level for HMGA2 and also at least one of the marker situations selected from the group consisting of nonincreased HbA1c blood values, nonincreased cholesterol values, nonincreased triglycerides, increased HDL cholesterol, nonincreased non-HDL cholesterol, nonincreased LDL cholesterol, nonincreased CRP, nonincreased blood sugar, nonincreased fasting blood sugar, nonincreased preprandial blood sugar, nonincreased postprandial blood sugar and age ≥45, and
- V) lowered nonincreased relative gene expression level for ADIPOQ, lowered relative gene expression level for HMGA2 and also at least one of the marker situations selected from the group consisting of nonincreased HbA1c blood values, nonincreased cholesterol values, nonincreased triglycerides, increased HDL cholesterol, nonincreased non-HDL cholesterol, nonincreased LDL cholesterol, nonincreased CRP, nonincreased blood sugar, nonincreased fasting blood sugar, nonincreased preprandial blood sugar, nonincreased postprandial blood sugar and age ≤45 are available it possible groups for the classification in step c).

Groups IV and V only contain individuals who have not formed the disease. Group III comprises individuals who are already showing clinical symptoms of T2D.

In case of doubt, the description "increased"/"lowered" means the following: For the relative gene expression levels, the following situation exists proceeding from the mean value of the patient population in question:

| | |
|---|---|
| +/−5% | unchanged |
| +5-10% | slightly increased |
| −5-10% | slightly lowered |
| +5-50% | increased |
| −5-50% | lowered |
| +/>50% | greatly increased |
| −/>50% | greatly lowered |

For the blood values, the grading applies accordingly, though the value reported in Table 1 applies here as reference value and only the range beyond the standard range is considered (thus, there are always either only "increased" or "lowered" values of the respective gradings in addition to the "unchanged" values.

Self-evidently, the patient population, which is the basis, always also comprises individuals who are already suffering from T2D.

For the division of the groups, reference is also made to the examples.

Part of the invention is also a kit for a method according to the invention, comprising
- a) a primer pair which binds to the cDNA of HMGA2 and
- b) a primer pair which binds to the cDNA of ADIPOQ and preferably
- c) a primer pair which binds to the cDNA of a housekeeping gene selected from the group consisting of HPRT, 18S rRNA, GAPDH, GUSB, PBGD, B2M, ABL, RPLP0.

Using said kit, it is possible to establish the gene expression levels of ADIPOQ and HMGA2 for the method according to the invention. The stated combination of primer pairs is thus suitable for a preferred variant of the method according to the invention.

The invention will be more particularly elucidated below on the basis of examples and taking the respective methodology into account.

Evaluation Method

Methodology

The goal of the methods used was to create new classifications (clusters) of diabetics and nondiabetics on the basis of various biomarkers such as, for example, HMGA2, ADIPOQ, IL-6 or PPAR gamma that expand the hitherto classifications diagnostically, but also—in future—therapeutically.

For the formal description of the study data, the customary methods of descriptive statistics were used. For nominal parameters, absolute frequency and relative frequency were specified, and for ordinal parameters, the median was additionally specified. For metric values, mean value and standard deviation were calculated. Normal distributions were tested with the aid of the Kolmogorov-Smirnov test (KS test). Nonparametric correlations between the biomarkers were calculated with the aid of Kendall's tau-b. For comparisons between categorical variables, the $X2$ test is was used:

To calculate the a priori unknown clusters, self-organizing maps (SOM) were used. SOMs (in this case, Kohonen maps by Teuvo Kohonen, cf. Teuvo Kohonen: Self-Organizing Maps. SpringerVerlag, Berlin 1995, ISBN 3-540-58600-8) are types of artificial neural networks having an unsupervised learning method with the goal of achieving a topographic feature map in the form of clusters of the input space (patient data). Here, patients within a cluster are intended to be maximally homogeneous and, between the clusters, maximally inhomogeneous. SOMs are used for clustering, for visualizing complex relationships, prediction (evaluation), modeling and data exploration. The network used here consists of 1000 neurons, correlations were automatically compensated and missing values were taken into account. To produce the clusters, the SOM-WARD clustering method was used (2-stage hierarchical cluster algorithm). Color codings were carried out using heat maps. The clusters produced as a result were compared descriptively. To describe the clusters with the aid of decision trees or facts and rules, various classification algorithms were used, such as C5.0, CART and Exhausted Chaid. As a measure of quality for the various classifiers, what were assessed were classification accuracy, compactness of the model (e.g., size of a decision tree), interpretability of the model, efficiency and robustness in the face of noise and missing values.

To further validate the models and to calculate the importance of the biomarkers for the various classification models, RBF networks (radial basis function networks) were created as a prediction model. The RBF networks yield a suitable approximation of the cluster allocation of the SOMs. The input vectors were normalized (subtraction of the mean value and division by the range (x−Min)/(Max−Min); normalized values are in the range between 0 and 1). The activation function used is the softmax function σ as normalized radial basis function. Softmax σ maps a k-dimensional vector z onto a k-dimensional vector σ(z).

The network performance (how "good" the network is) was checked on the basis of the following data:
  Model summary: Results including error, relative error or percentage of false predictions.
  Classification results: A classification table was specified for each dependent variable.
  ROC curves: ROC curves (Receiver Operating Characteristic curves) specify the sensitivity and specificity for each possible cut-point of the input variables. The Area under the Curve AUC is a measure of the quality of the classification, and also
  Cumulative gain charts.
  Specifically, the following methods were used:
  1. Self-organizing neural networks (→Kohonen maps)
  2. Classification algorithms
    Entropy-based learning methods (C5.0)
    Exhausted Chaid and
    CART
  3. Radial basis functions (specific type of neural networks)
  4. Descriptive and inductive statistics
1) Self-Organizing Neural Networks Self-organizing maps (SOM) refer to types of artificial neural networks having an unsupervised learning method with the goal of achieving a topological representation of the input space (in this case, patient data). The best-known SOMs are the topology-maintaining Kohonen maps by Teuvo Kohonen. The learning algorithm independently produces classifiers, according to which it divides the input patterns into (hitherto unknown) clusters. What is to be achieved as the goal is that the patients are maximally homogeneous within a cluster and maximally inhomogeneous between the clusters.

Core concept (topographic feature map): "Neighboring" input vectors (in this case, patient data) should belong to neighboring neurons in the map, with the result that the density and distribution of the neurons correspond to the probability model of the training quantity.

Advantages: Neighborhood relationships in the "confusing" input space can be directly read in the output layer.

Uses: SOMs are used for clustering, for visualizing complex relationships, prediction (evaluation), modeling and data exploration. Usage for the problems in the present case focuses on clustering, visualization and prediction.

(Tools: for example, Self Organizing Maps in R (R is a free programming language for statistical calculations and graphs. R is part of the GNU project, cf. also https://cran.r-project.org/web/packages/som/som.pdf and FIG. 1)

1.1) Formal Description of the Kohonen Network Model (Algorithm)

Figure 2:
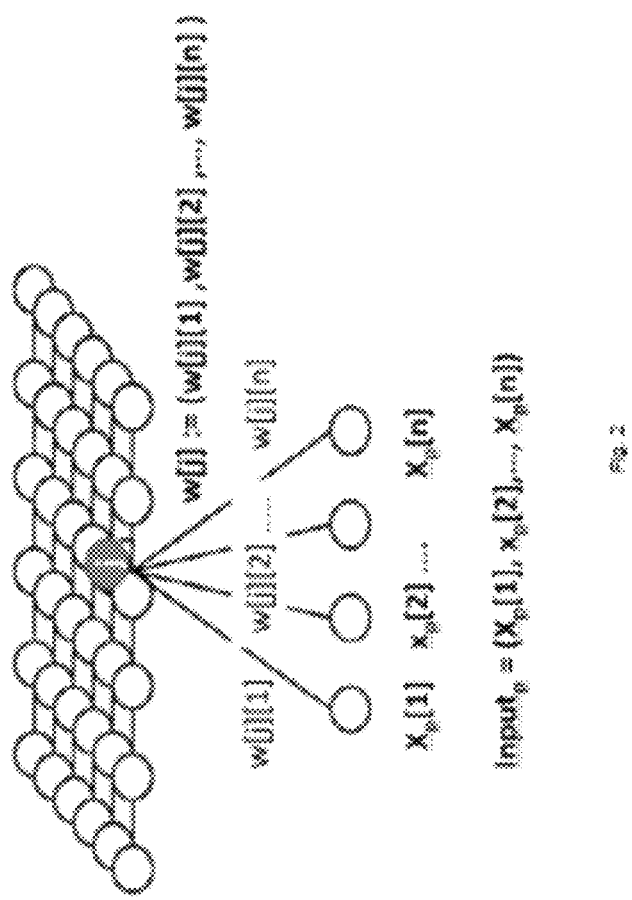

An SOM consists of two layers of neurons (input layer and output layer), cf. also FIG. 2.

Each neuron of the input layer is connected to each neuron of the output layer (the neurons of the input layer are completely networked with those of the output layer). Each neuron of the input layer corresponds to a parameter of the data set. The number of input neurons is the dimension of the input layer. The output neurons are related to one another by a neighborhood weighting function.

The strength of the connection is represented by a number (=weight) w[i][j]

(w[i][j] is the weight which specifies the strength of the connection between the i-th input neuron and the j-th output neuron). The vector w[j] represents all weights w[i][j] (i=1 . . . n, n is the number of parameters acquired for each patient) in relation to the j-th output neuron. Input vectors and weight vectors are normalized (length=1).

Initialize the weight vectors. Arbitrary values produced by a random generator are specified for the weights as start default.

Each patient p defines, by the values thereof, an input vector $Input_p = (x_p[1], x_p[2], \ldots, X_p[n])$ with the components $Input_p[i] = x_p[i]$. These input vectors are first normalized to 1.

For each patient p and each neuron j in the output layer, the Euclidean distance $$s_p[j] = \|w[j] - input_p\| = \sqrt{\sum_i (w[j][i] - input_p[i])^2}$$

between the weight vector w[j] and the input vector $Input_p$ is calculated.

The output neuron which has the smallest distance to the input vector $Input_p$ is called the winner neuron ("winner takes all"). The weight vector of the winner neuron is most similar to the input vector, i.e., it has the "maximum stimulation" under the input vector $Input_p$. If 2 or more output neurons should have the same minimum distance, one neuron is selected by a random generator.

The winner neuron and its neighbors are awarded the "contract", i.e., may represent the input A function $f(input_p)$ is hereby defined which assigns a location α in a representative layer (map) to each vector $input_p$ of the input space (pattern space, feature space)

f: $input_p \rightarrow (input_p) = \arg\min(\|w[j] - input_p\|)$. The minimum is formed over all weight vectors w[j]. The function arg provides the index of the winner neuron.

Determine for each patient (input pattern) the winner neuron according to the above instructions.

Neighborhood weighting function and weight adaption: In the next step, the weights of the winner neuron and those of its surrounding neurons are adapted. In this case, the degree of neighborliness in relation to the winner neuron plays a large role.

Let us assume the winner neuron has the index $\alpha$. For an input[i] and an output neuron j, Dw[j][i] refers to the weight change in the context of a learning rule. This is calculated as follows:

$$Dw[j][i]=\eta(t)*(\text{input}[i]-w[i][j])*NbdWt(\alpha,j)$$

where $\eta(t)$ refers to the learning rate ($\eta(t)$ where $0<\eta(t)<1$) and NbdWt($\alpha$, j) refers to the neighborhood weighting function. A neighborhood weighting function calculates the degree of neighborliness of an output neuron in relation to the winner neuron, which is between 0 and 1. Convergence evidence against a statistically describable equilibrium state exists for, for example, $\eta(t):=\eta*t^{-a}$ where $1<a\leq1$.

Approximate weight vectors to one another proportionally to the neighborhood weighting function The weight vectors w[j] of all neurons j are updated according to the neighborhood weighting function NbdWt($\alpha$, j) of the neuron $\alpha$. The new weight $w_{new}$[i][j] is calculated as follows:

$$w_{new}[j][i]:=w[j][i]+Dw[j][i]$$

The neighborhood weighting function can, for example, be one of the following functions:

$$NbdWt(\alpha, j) = \frac{1}{1+\left(\frac{d(\alpha, j)}{s}\right)^2}$$

$$NbdWt(\alpha, j) = e^{-\left(\frac{d(\alpha, j)}{s}\right)^2}$$

where $d(\alpha, j):=(\alpha-j)$; s is a scalar. The width s=s(t) of the neighborhood weighting function and the learning step width $\eta(t)$ are reduced overtime: The winner neuron and its neighbors are "activated" according to the function NbdWt($\alpha$, j).

Normalize weight vectors to a length of 1, present next data point.

For the various methods for map color codings (heat maps), reference is made to the literature (e.g., http://citeseerx.ist.psu.edu/viewdoc/download?doi=10.1.1.100.500&rep=rep1&type=pdf, https://arxiv.org/pdf/1306.3860.pdf or https://www.visualcinnamon.com/2013/07/self-organizing-maps-creating-hexagonal.html).

2) Classification Algorithms

To evaluate the SOM models (description of the classes by facts and rules or decision trees), 3 different classification algorithms are used: (1) Entropy-based learning methods (C5.0), (2) Exhausted Chaid and (3) CART.

2.1) Definition

Classification methods are methods and criteria for classifying objects (in this case, patients) into classes (in this case, types and subtypes of healthy prediabetics and diabetics).

From a training quantity of examples having known class affiliation, a classifier in the form of decision trees or equivalent in the form of facts and "If-Then" rules is generated with the aid of the classification algorithm. Classification is differentiated from clustering (see also SOMs) in that the classes are a priori known in classification, whereas the classes must first be sought in clustering.

Decision trees serve for decision making by means of an arboreal structure consisting of a root node (start node), nodes, edges and leaves (end nodes) (FIG. 2).

Formally, a tree is a finite graph having the properties:
1) There is exactly one node in which no edge ends (the "root").
2) Exactly one edge ends in each node different from the root, the edges are directed
3) Each node is reachable from the root on exactly one path.

A decision tree is a tree:
1) Each node tests an attribute
2) Each branch corresponds to an attribute value
3) Each leaf (node without outgoing edges) assigns a class.

Figure 3:
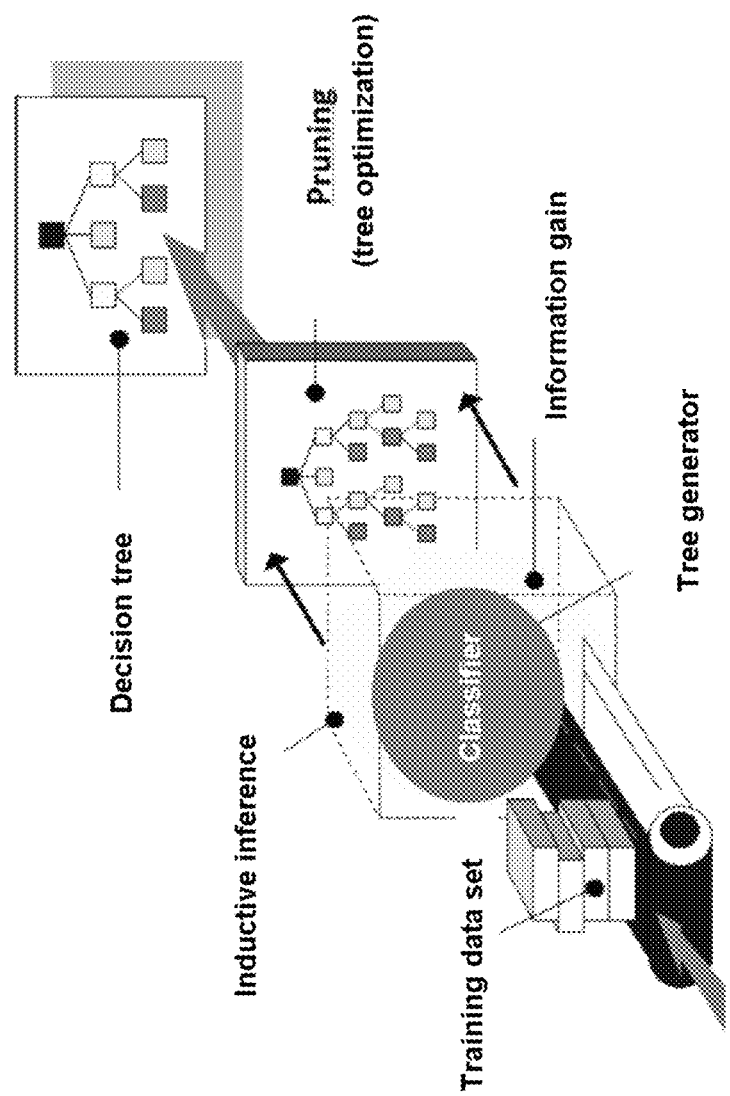

FIG. 3 shows the formal components of a classification algorithm.

Figure 4:
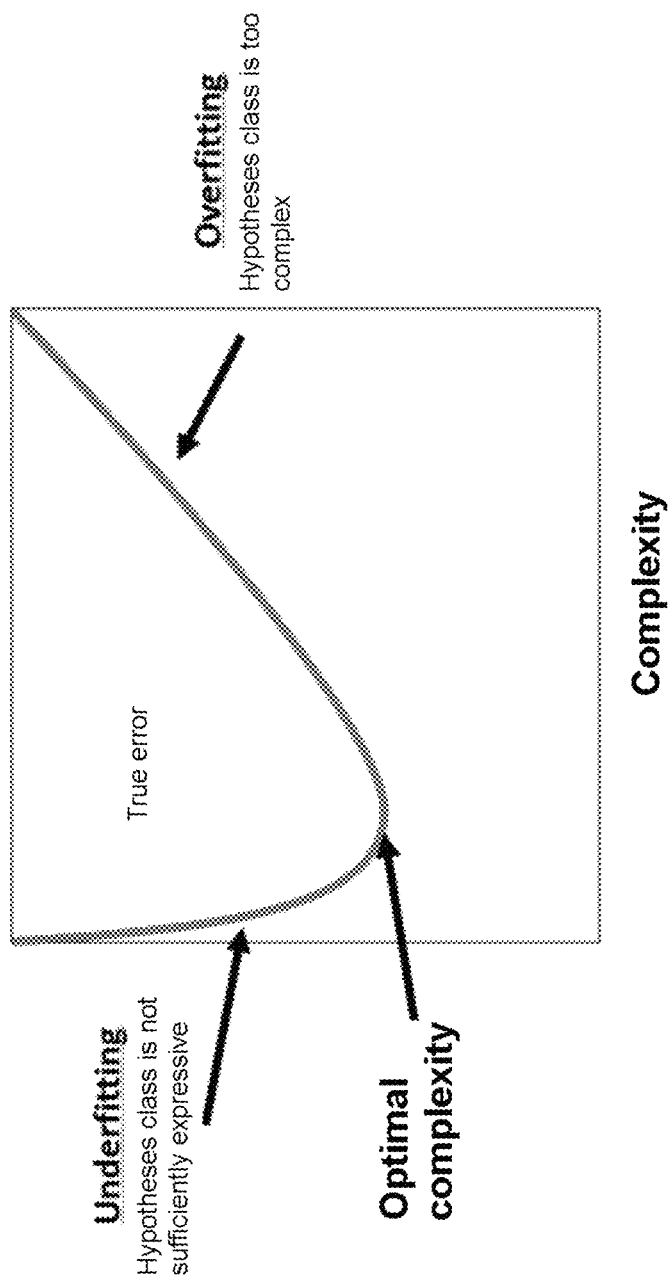

Problem: The classifier is optimized for the training data in the first step. It may possibly provide relatively poor results (underfitting or overfitting: hypothesis class is too inexpressive or too complex) on the data population, cf. FIG. 4.

A possible overfitting can be reduced by pruning or boosting methods; in this case, a person skilled in the art chooses the number of required iteration steps to improve group formation.

In general, the quantity of available examples is divided into two subquantities (train-and-test).
  Training quantity: for the learning of the classifier (construction of the model)
  Test quantity: for the assessment of the classifier If this is not usable because the quantity of objects having known class affiliation is small, the so-called m-fold cross-validation is used instead of train-and-test.

The following criteria are taken as measures of quality for classifiers:
  Classification accuracy
  Compactness of the model (e.g., size of a decision tree)
  Interpretability of the model
  Efficiency
  Robustness in the face of noise and missing values 2.2) Construction of Decision Trees
  (See also
  Quinlan, J. Ross (1986): Induction of decision trees. In: Machine Learning 1 (1), pages 81-106.
  Quinlan, J. Ross (1993): C4.5. Programs for machine learning. In: J. Ross Quinlan. San Mateo, Calif.: Morgan Kaufmann (The Morgan Kaufmann series in machine learning).
  Quinlan, J. Ross (1996): Improved use of continuous attributes in C4. 5. Journal of artificial intelligence research 4, pages 77-90.)

Basis Algorithm
Loop:
  1. Choose the "best" decision attribute A for the next node
  2. For each value of A, generate a new child node
  3. Assign the training data to the child nodes
  4. If the training data are classified without errors, then STOP. Otherwise, iterate over child nodes ($\rightarrow$1.).

Designations:
  Training data set T,
  Number of training data |T|,
  Classes $C_i$: The data set of all training data in the class $C_i$. $|C_i|$ is the number of elements in class $C_i$. The following is valid: $\Sigma|C_i|=|T|$ (i=1, . . . k).

Attribute $A=\{a_1, a_2, \ldots, a_m\}$. Attribute A subdivides the data set T into m subsets
$T_1, T_2, \ldots, T_m$. $|T_i|$ is the number of subquantity $T_i$.
Given training data set T and attributes A;
Output: Information gain (T, A) of attributes A for the training data set T
3) Algorithm (Calculation of Information Gain with the Aid of Entropy Using the Example of ID3)
The empirical entropy for a quantity T of training objects having the classes $C_i$ (i=1, ..., k) is defined as $$\text{entropy }(T) = \sum_{i=1}^{k} p_i \cdot \log p_i$$

where $p_i := |C_i|/|T|$

The attribute A has produced the partitioning $T_1$, $T_2$, ..., $T_m$. The empirically determined entropy G(T,A) for a quantity T and an attribute A is defined as $$G(T, A) = \sum_{i=1}^{m} \frac{|T_i|}{|T|} \cdot \text{entropy }(T_i)$$

The information gain Gain(T, A) due to the attribute A in relation to T is defined as $$\text{Gain}(T, A) = \text{entropy }(T) - G(T, A) = \text{entropy }(T) - \sum_{i=1}^{m} \frac{|T_i|}{|T|} \cdot \text{entropy }(T_i)$$

Input: Training data set T having the classes $C_i$ (i=1, ..., k), attributes A and threshold $\epsilon$;
Output: Decision tree E;
Algorithm:
1. Creation of a node K;
2. If all example data in T have an identical class $C_j$ or the number of data is smaller than threshold $\epsilon$, the single node is back as a leaf with class $C_j$ in relation to node K;
3. If $A=\emptyset$, the single node is assigned as a leaf with the most common class in T in relation to node K;
4. Calculation of the information gain of A in T and determination of the best attribute $A_g$ with maximum information gain on the basis of $$\text{Gain}(T, A) = \text{entropy }(T) - G(T, A) = \text{entropy }(T) - \sum_{i=1}^{m} \frac{|T_i|}{|T|} \cdot \text{entropy }(T_i)$$

5. Designation of node K with $A_g$
6. For all attribute values $A_{gj}$ of $A_g$, calculate the sub-data set $T_{gi}$ of all examples from the training data set with $A_{gj}$
7. If $T_{gi}=\emptyset$, a leaf with the most common class in relation to node K is added, otherwise
8. Recursion of the branch of $A_g$.
Note:
For a random event y which occurs with probability P(y), the following applies:

Information content: $h(y) = -\log_2(P(y))$

The entropy is the average value of the information content of the random variable y $$H[y] = \Sigma_y P(y) h(y) = -\Sigma_y P(y) \log 2(P(y))$$

Classification Algorithms Used
ID3
Discrete attributes, no missing attributes
Information gain as measure of quality.
C4.5/C5.0
Extension of ID3
Information gain ratio as measure of quality. Missing attributes
Numerical and real-valued attributes
Pruning of the decision tree
The information gain ratio is defined as $$\text{GainRatio}(T, A) := \frac{\text{Gain}(T, A)}{\text{SplitInformation}(T, A)}$$

$$\text{SplitInformation}(T, A) = -\sum_{i=1}^{m} \frac{|T_i|}{|T|} \cdot \log_2\left(\frac{|T_i|}{|T|}\right)$$

CART (Classification and Regression Trees)
See also Hastie, T., Tibshirani, R., Friedman, J. H. (2001). *The elements of statistical learning: Data mining, inference, and prediction.* New York: Springer Verlag.
Method analogous to ID3 or C5.0. The measure of information is defined by the Gini index. The Gini index is minimized (instead of maximizing the Gini gain).
Gini Gain $$\text{Gini}(T, A) = \sum_{i=1}^{k} \frac{T_i}{T} \cdot \text{Gini}(T_i)$$

where $$\text{Gini}(T) = 1 - \sum_{i=1}^{k} p_i 2$$

$P_i$ is the relative frequency of the class $C_i$ in T
CHAID (Chi-Square Automatic Interaction Detectors)
See also Sonquist, J. A. and Morgan, J. N. (1964): The Detection of Interaction Effects. Survey Research Center, Institute for Social Research, University of Michigan, Ann Arbor.
CHAID is a further algorithm for constructing decision trees. The differences in relation to C5.0 or CART are that the chi-square test of independence is used to choose the attributes in the CHAID algorithm and that the CHAID algorithm stops the growth of the tree before the tree has become too large. The tree is thus not left to grow at will in order to shorten it afterwards with a pruning method.
4) Radial Basis Function Networks (RBF Networks)
See also Zell, A.: "Simulation neuronaler Netze" [simulation of neural networks]. Oldenbourg 1994
To further validate the models and to calculate the importance of the biomarkers for the various classification models, RBF networks are used. RBF networks create prediction models. They are particularly suitable for the approximation of functions.
The RBF network consists of an input layer having n neurons, a hidden layer having k neurons and an output layer having m neurons. An n-dimensional pattern is mapped thereby into an m-dimensional output space.

Figure 5:
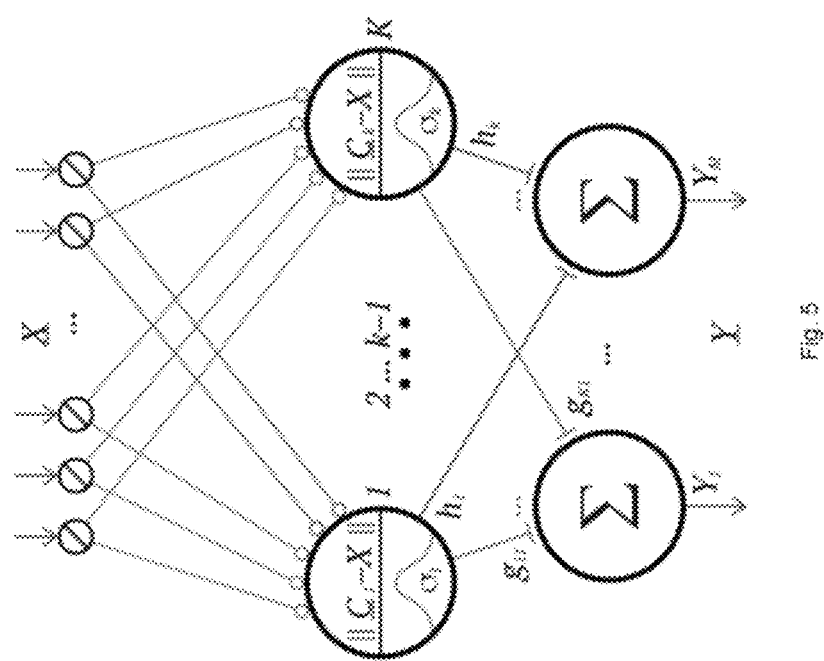

The input layer is purely a forwarding means. Each neuron distributes its value to all hidden neurons. In the hidden layer, in each neuron, the distance between the input and the center c is formed with the aid of a Eucledean norm. Radial basis functions are used as network input and activation function (cf. FIG. 5).

The activation function of each hidden neuron is a so-called radial function,
i.e., a monotonically decreasing function $$f: IR_0^+ \to [0, 1] \text{ where } f(0) = 1 \text{ and } \lim_{x \to \infty} f(x) = 0 \text{ m}$$

The input vectors are normalized (subtraction of the mean value and division by the range (x−Min)/(Max−Min); normalized values are in the range between 0 and 1). The activation function used is the softmax function σ as normalized radial basis function. Softmax σ maps a k-dimensional vector z onto a k-dimensional vector σ(z).

$$\sigma(z)_j = \frac{e^{z_j}}{\sum_{k=1}^{K} e^{z_k}}, j = 1, \dots, k$$

The number of neurons in the hidden layer is determined by the "Bayesian Information Criterion" (cf. Schwarz, Gideon E. (1978), "Estimating the dimension of a model", Annals of Statistics 6 (2): 461-464, MR 468014, doi: 10.1214/aos/1176344136) (BIC). The best number of hidden units is that which yields the smallest BIC on the basis of the training data.

For the output layer, we used the identity function as activation function. Thus, the output units are singly weighted sums of the hidden units. The output of the network is therefore a linear combination of the radial basis functions of the inputs and the weights.

Network Performance

Network performance checks how "good" the network is. To this end, a series of results is provided.

Model summary.

Results including error, relative error or percentage of false predictions and training time.

Classification results.

A classification table is specified for each categorical dependent variable.

ROC curves.

The ROC curves (Receiver Operating Characteristic curves) specify the sensitivity and specificity for each possible cut-point of the input variables. The Area under the Curve AUC is a measure of the quality of the classification.

Cumulative gain charts.

EXAMPLES

The following examples are based on two different patient populations. Patient population 1 was used as the basis for Examples 1 and 3 which follow. It is distinguished by a number of 7 individuals, 4 of which had T2D, and patient population 2, the basis for Examples 2, 4 and 5, consisted of 61 subjects, 26 of which had T2D.

A sample having the following $\Delta C_T$ was used as calibrator for the relative gene expression values:
Patient population 1 and 2: HMGA2: 6.513
ADIPOQ: 5.484

In this case, the $\Delta C_T$ values are the $C_T$ value of the target gene minus the $C_T$ value of the endogenous control (housekeeping gene), the $C_T$ value in each case being the value at which, during amplification, the signal for the respective cDNA first exceeds the threshold.

The following mean values resulted for the mean values of the relative gene expression in patient population 2:
HMGA2: 1.663117
ADIPOQ: 0.95365

Example 1

Detection of the Expression of ADIPOQ and HMGA2 in Adipose Tissue Puncture Biopsies, Obtained by Fine-Needle Aspiration of Subcutaneous Abdominal Adipose Tissue Materials and Methods Fine-Needle Aspiration Fine-needle aspirates were obtained by puncture of subcutaneous abdominal hWAT by means of a 20 ml syringe and a disposable injection cannula (diameter 0.90×40 mm). After disinfection of the puncture site, the cannula was inserted into the subcutaneous adipose tissue. Using the syringe, a negative pressure was generated, and the cannula was moved back and forth in the tissue in a fan-shaped manner in order to thus aspirate cells of the adipose tissue. Directly after the puncture procedure, the samples were gathered in 1 ml of QIAzol Lysis Reagent (QIAGEN, Hilden, Germany) and the cannula was flushed multiple times with the QIAzol. Thereafter, the samples were frozen at −80° C.

RNA Isolation

Total RNA was isolated by means of an RNeasy Lipid Tissue Mini Kit (QIAGEN, Hilden, Germany) in a QIAcube (QIAGEN, Hilden, Germany) according to the manufacturer's instructions. The fine-needle aspirates (5 mg) in 1 ml of QIAzol Lysis Reagent were homogenized in a Tissue Lyser II (QIAGEN, Hilden, Germany) and the homogenate was subsequently incubated at room temperature for 5 min. This was followed by the addition of 200 μl of chloroform, which was mixed with the sample by vigorous shaking by hand for 15 sec. The sample was incubated again at room temperature for 2 min and centrifuged at 12 000×g for at 4° C. for 15 min. Thereafter, the upper aqueous phase was transferred to a fresh 2 ml cup and the total RNA was isolated over a Qiagen RNeasy Mini Spin column (QIAGEN, Hilden, Germany) in a QIAcube according to the manufacturer's instructions.

cDNA Synthesis

For the cDNA synthesis, ≤250 ng of RNA was transcribed into cDNA by means of 200 U of M-MLV reverse transcriptase, RNase Out (Thermo Fisher Scientific, Darmstadt, Germany) and 150 ng of random primer (Thermo Fisher Scientific, Darmstadt, Germany) according to the manufacturer's instructions. The RNA was denatured at 65° C. for 5 min and subsequently stored on ice for at least 1 min. After the addition of the enzyme, the mix was incubated at 25° C. for 10 min for the annealing of the random primers to the RNA. The subsequent reverse transcription was carried out at 37° C. for 50 min, followed by a 15 min inactivation of the reverse transcriptase at 70° C.

Preamplification of the cDNA

5 μl of cDNA was preamplified by means of RealTime ready cDNA Preamp Mastermix (Roche, Mannheim, Germany) using HMGA2 and HPRT (hypoxanthine phosphoribosyltransferase 1) specific primers according to the manufacturer's instructions. These gene-specific primers appropriately bind to the respective cDNA, with the result that the amplicons generated contain the binding sites of the primers of the gene-specific assays used in the quantitative real-time PCR. The cDNA was preamplified according to the following temperature profile: 95° C. for 1 min followed by 14 cycles at 95° C. for 15 sec and at 60° C. for 4 min.

Quantitative Real-Time PCR (qRT-PCR)

The relative quantification of gene expression was carried out by means of real-time PCR on the Applied Biosystems 7300 Real-Time PCR System. Commercially available gene expression assays (Life Technologies, Carlsbad, CA, USA) were used for the quantification of the mRNA level of HMGA2 (assay ID Hs00171569_m1) and ADIPOQ (assay ID Hs00605917_m1). As described by Klemke et al. (Klemke M, Meyer A, Hashemi Nezhad M, Beige G, Bartnitzke S, Bullerdiek J (2010) Loss of let-7 binding sites resulting from truncations of the 3' untranslated region of HMGA2 mRNA in uterine leiomyomas. Cancer Genet Cytogenet 196:119-123), HPRT was used as endogenous control. All measured samples were determined in triplicate. Gene expression was quantified in 96-well plates containing the preamplified cDNA to be investigated, the respective gene-specific assay and the FastStart Universal Probe Master (Rox) (Roche, Mannheim, Germany). The temperature profile of the real-time PCR followed the manufacturer's instructions: The template is denatured at 95° C. for 10 min. This was subsequently followed by amplification in 50 cycles, starting with denaturation at 95° C. for 15 sec and the combination of annealing/elongation at 60° C. for 60 sec. The data obtained were evaluated by means of a comparative delta Ct method (ΔΔCT method). [(Livak K J, Schmittgen TD (2001) Analysis of relative gene expression data using real-time quantitative PCR and the $2^{-\Delta\Delta C(T)}$ Method. Methods 25: 402-408)].

Result

Figure 6:
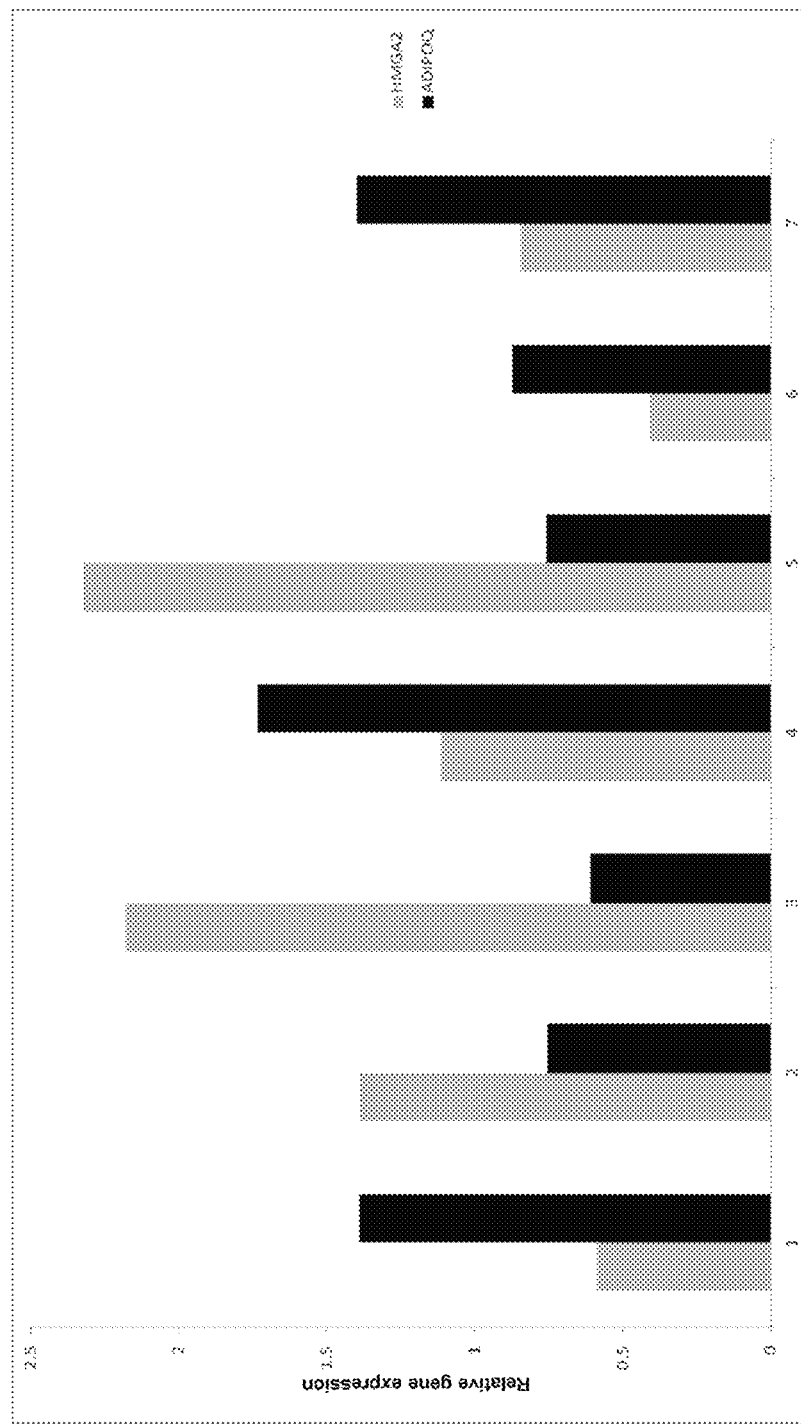

By means of qRT-PCR, it was possible to measure the gene expression of ADIPOQ and HMGA2 in seven samples from human patients (FIG. 6). The results clearly show that ADIPOQ and HMGA2 mRNAs are reliably quantifiable from fine-needle aspirates with even very small amounts of adipose cells. Moreover, the amount of isolated RNA from the fine-needle aspirates is sufficient for determining the expression of further genes after a preamplification.

FIG. 6 depicts the relative expression of HMGA2 and ADIPOQ in seven samples. It shows that a reliable quantification of HMGA2 and ADIPOQ expression is possible even from very small amounts of RNA (concentration ≤25 ng/µl) obtained by fine-needle aspiration. Moreover, FIG. 6 shows that the expression of the genes varies between the individual samples and that inter-individual differences are thus detectable.

Example 2

The Expression of ADIPOQ in Adipose Tissue Samples from Type 2 Diabetics and Nondiabetics Materials and Methods Tissue Samples The human subcutaneous abdominal adipose tissues were collected during operations and stored in liquid nitrogen after the operation. Thereafter, the samples were frozen at −80° C. For all human adipose tissue samples used, the requirements of the Declaration of Helsinki were met. A written declaration of consent for the use of tissue samples was returned by the patients (n=61).

RNA Isolation

Total RNA was isolated by means of an RNeasy Lipid Tissue Mini Kit (QIAGEN, Hilden, Germany) in a QIAcube (QIAGEN, Hilden, Germany) according to the manufacturer's instructions. The adipose tissue samples (50-100 mg) in 1 ml of QIAzol Lysis Reagent were homogenized in a Tissue Lyser II (QIAGEN, Hilden, Germany) and the homogenate was subsequently incubated at room temperature for 5 min. This was followed by the addition of 200 µl of chloroform, which was mixed with the sample by vigorous shaking by hand for 15 sec. The sample was incubated again at room temperature for 2 min and centrifuged at 12 000×g for at 4° C. for 15 min. Thereafter, the upper aqueous phase was transferred to a fresh 2 ml cup and the total RNA was isolated over a Qiagen RNeasy Mini Spin column (QIAGEN, Hilden, Germany) in a QIAcube according to the manufacturer's instructions. The RNA concentration was determined by means of a photometer and the samples were subsequently stored at −80° C.

cDNA Synthesis

For the cDNA synthesis, 250 ng of RNA was transcribed into cDNA by means of 200 U of M-MLV reverse transcriptase, RNase Out (Thermo Fisher Scientific, Darmstadt, Germany) and 150 ng of random primer (Thermo Fisher Scientific, Darmstadt, Germany) according to the manufacturer's instructions. The RNA was denatured at 65° C. for 5 min and subsequently stored on ice for at least 1 min. After the addition of the enzyme, the mix was incubated at 25° C. for 10 min for the annealing of the random primers to the RNA. The subsequent reverse transcription was carried out at 37° C. for 50 min, followed by a 15 min inactivation of the reverse transcriptase at 70° C.

Quantitative Real-Time PCR (qRT-PCR)

The relative quantitative real-time PCR was carried out as described in Example 1.

Result

Figure 7:
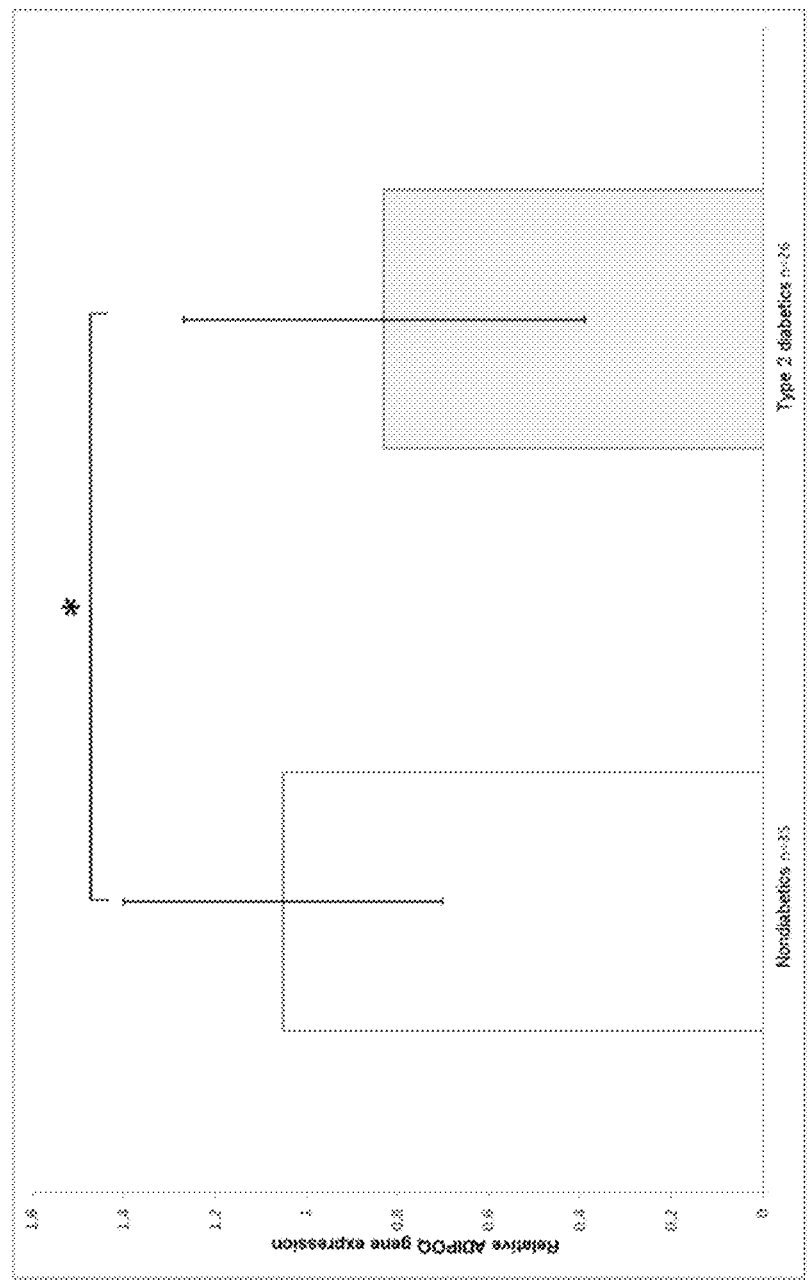

The differences in the level of adiponectin in the blood plasma of type 2 diabetics and nondiabetics, as described in the literature, can also be demonstrated at the level of gene expression of ADIPOQ in the adipose tissue of type 2 diabetics and nondiabetics (FIG. 7). FIG. 7 shows the significant difference ($p<0.05$) in the relative gene expression of ADIPOQ in the adipose tissue of 35 nondiabetics and 26 type 2 diabetics.

Example 3

Differing ADIPOQ Gene Expression in Adipose Tissue Puncture Biopsies from Type 2 Diabetics Materials and Methods Sample Preparation The sample preparation was carried out by means of fine-needle aspiration as described in Example 1. The following sample-processing steps, i.e., RNA isolation, cDNA synthesis, preamplification of the cDNA and quantitative real-time-PCR, were also carried out as described in Example 1.

Result

Figure 8:
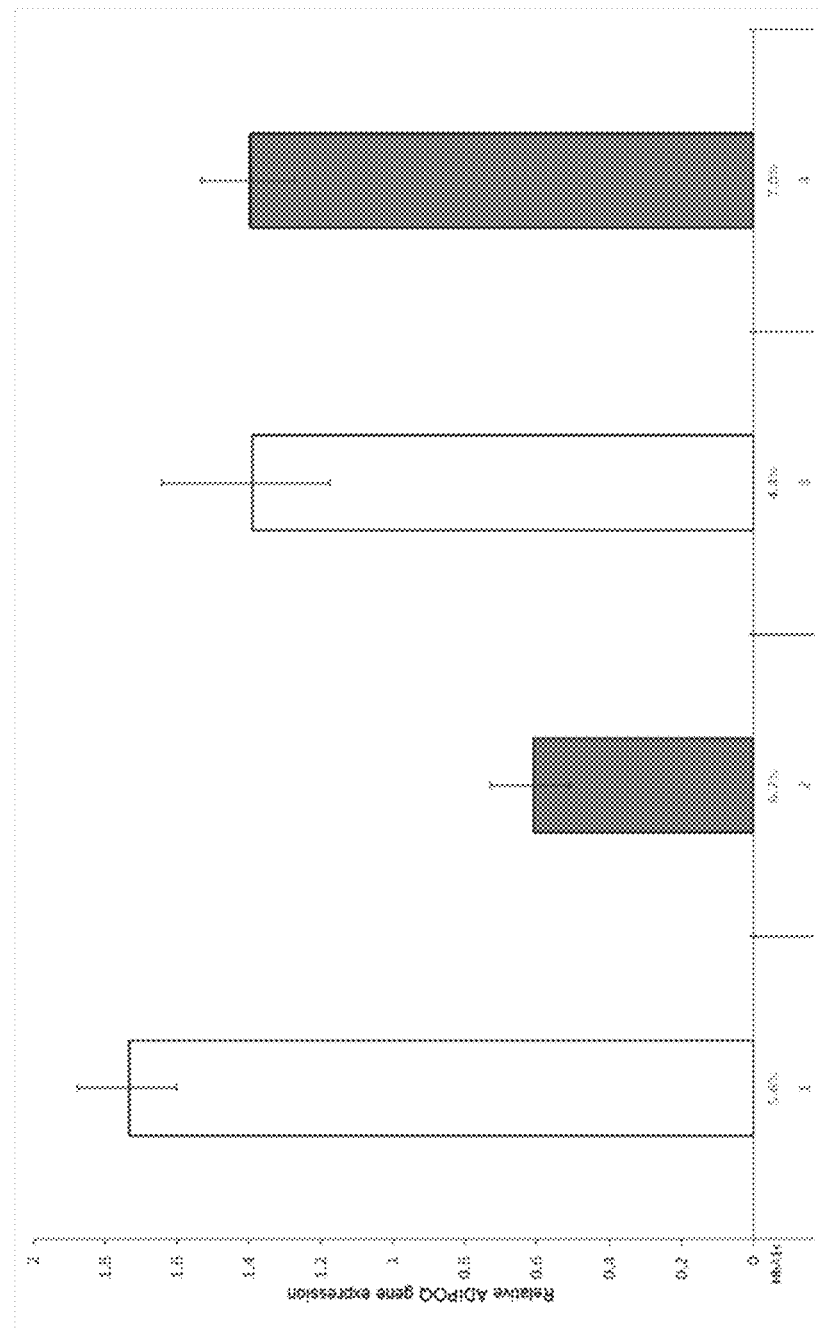

FIG. 8 shows the expression of ADIPOQ in adipose tissue puncture biopsies from four patients. Patients 2 and 4 have an HbA1c value of 6.7% and 7.0%, respectively, and are therefore diabetics; patients 1 and 3 are nondiabetics (HbA1c values of 5.6% and 4.4%, respectively). The measured ADIPOQ gene expression values are 1.734 for patient 1, 0.609 for patient 2, 1.389 for patient 3 and 1.397 for patient 4. The measured gene expression levels of ADIPOQ in samples from human patients show (FIG. 8) that, surprisingly, type 2 diabetics such as patient 4 can also have a high level of ADIPOQ expression. This result could not be expected from the current literature. The differing ADIPOQ expression in patients 2 and 4 would also mean a different form of therapy with respect to, for example, the administration of oral antidiabetic agents. The protein adiponectin encoded by the ADIPOQ gene suppresses hepatic gluconeogenesis via the receptor AdipoR1 and stimulates glucose uptake in skeletal muscle via the receptor AdipoR2. Therefore, the administration of drugs from the group consisting of biguanide and biguanide derivatives (e.g., metformin) would not be advisable in the case of high ADIPOQ expression values, since this group of active ingredients inhibits hepatic gluconeogenesis and improves peripheral insulin action, i.e., the mode of action of biguanide and biguanide derivatives is similar to that of adiponectin. By contrast, in the case of low ADIPOQ expression values, the administration of biguanide or biguanide derivatives might (possibly) be advisable in order to thus compensate for the relative adiponectin deficiency.

Example 4

Figure 9:
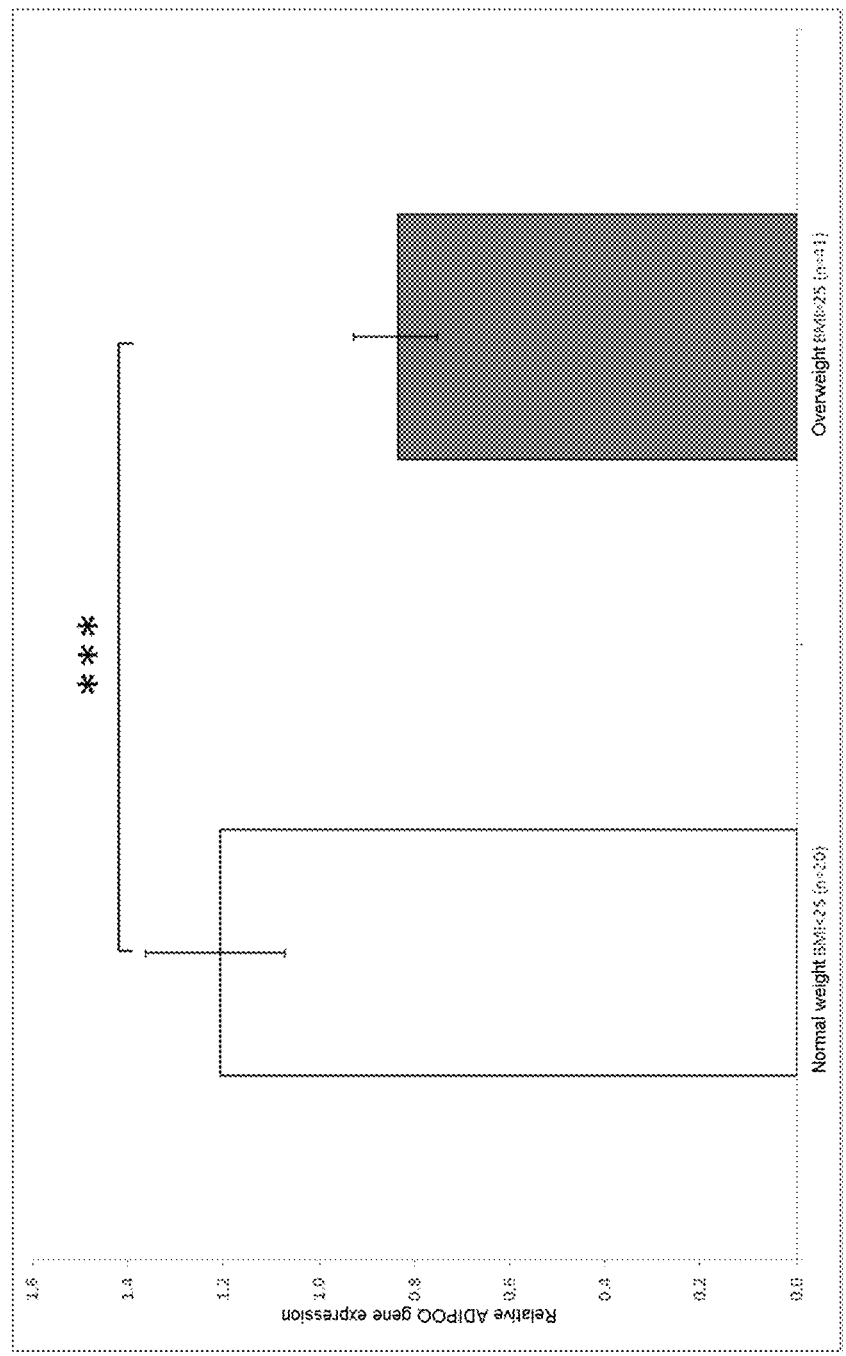
Figure 10:
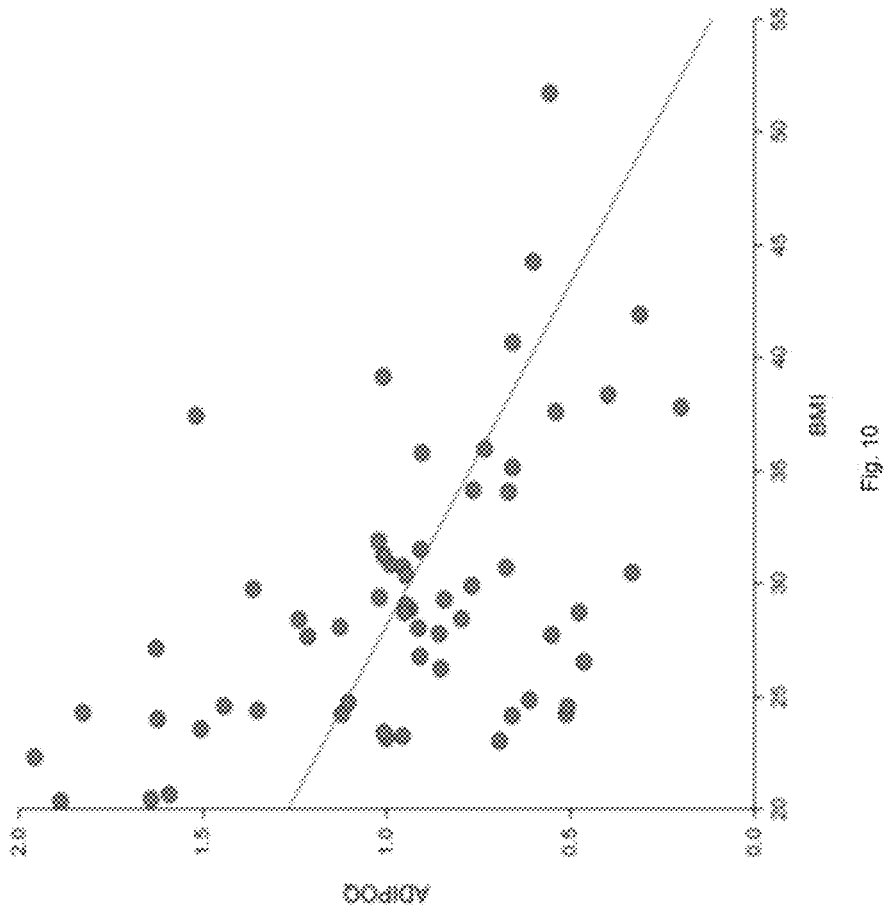
Figure 11:
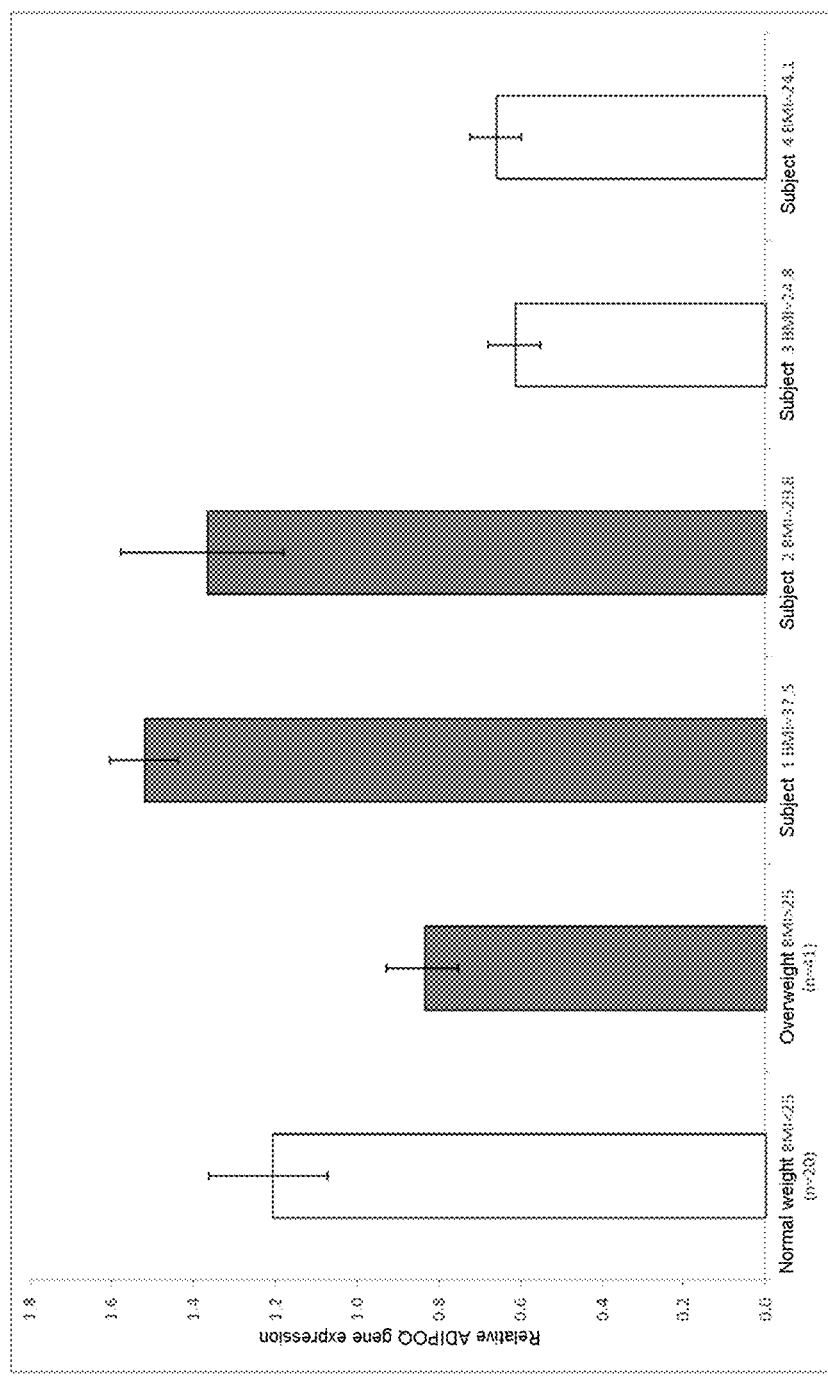
Figure 12:
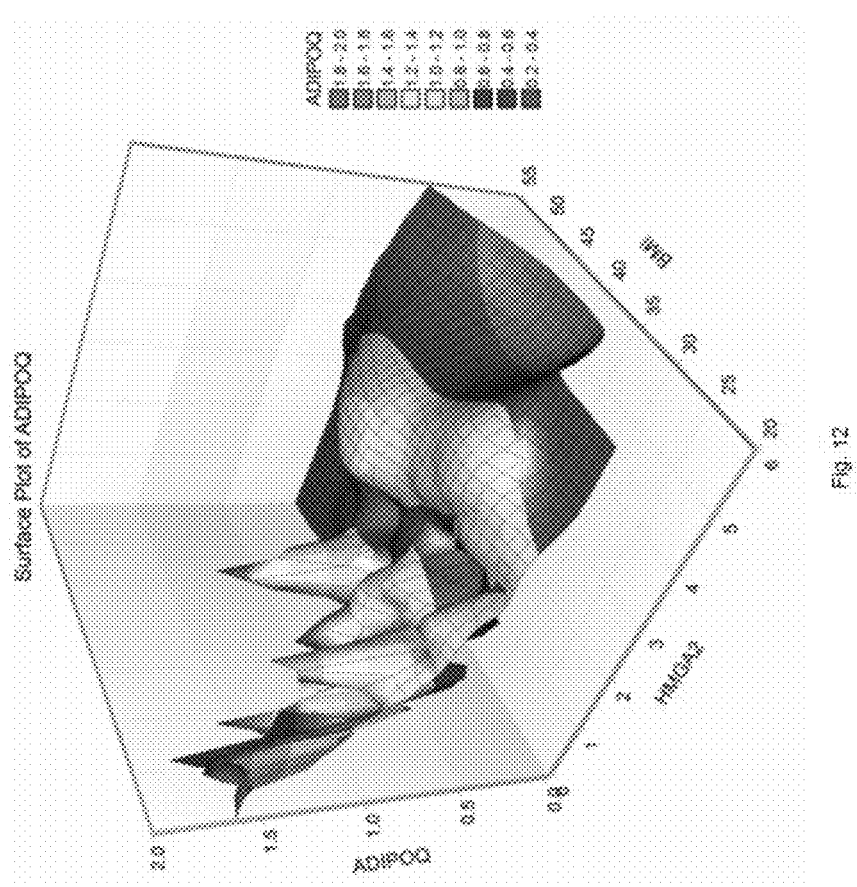
Figure 13:
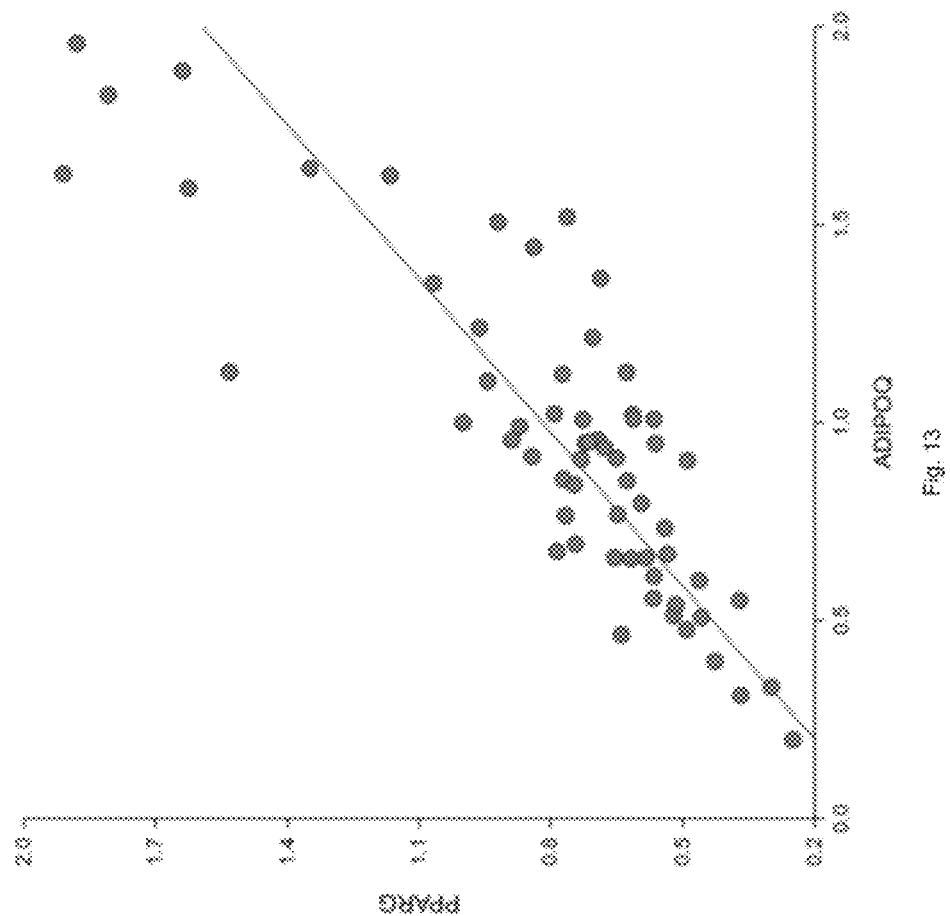

ADIPOQ Gene Expression in Adipose Tissue Samples from Normal-Weight and Overweight Individuals
Materials and Methods
Sample Preparation The adipose tissue samples were obtained during operations as described in Example 2. The following sample-processing steps, i.e., RNA isolation, cDNA synthesis, and quantitative real-time-PCR, were also carried out as described in Example 2.
Result FIG. 9 shows the expression of ADIPOQ in adipose tissue samples from 20 normal-weight patients (BMI<25) and 41 overweight patients (BMI≥25). The gene expression level of ADIPOQ in the normal-weight group was 1.207 and was highly significantly greater (p<0.001) than the ADIPOQ expression level in the overweight group at 0.834. The analysis of the correlation between ADIPOQ expression and BMI in 61 patients showed a moderate (−0.507) and highly significant (p<0.001) inverse relationship (FIG. 10). This result is basically consistent with the inverse relationship between blood-plasma adiponectin level and body weight, as described in the literature. However, if the ADIPOQ gene expression in overweight or obese individuals and in normal-weight individuals is compared with the ADIPOQ expression in the total patient population (see FIG. 11), it becomes apparent that, surprisingly, there are exceptions among the inverse relationship between blood-plasma adiponectin level and body weight. FIG. 6 shows that the male subject 1 with a BMI of 37.5 and the female subject 2 (BMI=29.8) have an ADIPOQ expression level of 1.519 and 1.364, respectively, which is more in line with the ADIPOQ expression level of the normal-weight group at 1.207. Moreover, the normal-weight male subjects 3 (BMI=24.8) and 4 (BMI=24.1) show an ADIPOQ expression level of 0.612 and 0.659, respectively, which is in the region of the ADIPOQ expression level of the overweight individuals at 0.834. These data suggest that the inverse correlation between ADIPOQ expression and BMI additionally corresponds with a further factor. Patent specification DE10 2015 208 083 B3 discloses a relationship between HMGA2 expression level and BMI. An analysis of the ADIPOQ and HMGA2 expression levels and BMI by means of a surface plot, as depicted in FIG. 12, shows that the correlation between ADIPOQ expression level and BMI is dependent on the HMGA2 expression level. This relationship could not be expected from the available scientific data and the prior art. Patent specification DE10 2015 208 083 B3 discloses moreover a correlation between high HMGA2 expression levels, low PPAR gamma expression levels and a high BMI. Since peroxisome proliferator-activated receptor gamma (PPAR gamma) regulates adipokines, such as, inter alia, adiponectin, the gene expression of PPAR gamma and ADIPOQ was examined. What became apparent was, as depicted in FIG. 13, a strong (0.838) and highly significant (p<0.001) correlation between the gene expression of PPAR gamma and ADIPOQ.

Example 5

Data Analysis by Means of Self-Organizing Maps Show Five Different Clusters Within the Patient Population
Materials and Methods
Sample Preparation The adipose tissue samples were obtained during operations as described in Example 2. The following sample-processing steps, i.e., RNA isolation, cDNA synthesis, and quantitative real-time-PCR, were also carried out as described in Example 2.
Statistical Analysis
See Methodology above
Result Various studies in the past have shown that low blood adiponectin levels are associated with an increased incidence of type 2 diabetes (T2D). Adiponectin is considered to be a "protective factor" against T2D and coronary heart disease, and high levels of the hormone are seen as an indicator of a lower risk of disease. However, as shown by Examples 3 and 4, high ADIPOQ expression levels can also be found in patients who have T2D and are overweight. There findings could not be expected from the available scientific data and thus have potential impacts on treatment of these patients. For a personalized treatment of, for example, T2D patients to be made possible, it is useful to identify the specific subtype of T2D from which the patient is suffering. A specific T2D subtype might, for example, be associated with insulin resistance, and another subtype might be associated with problems in insulin secretion. To identify these T2D subtypes, what can help according to the invention is the analysis of the relationship of the biomarkers ADIPOQ, HMGA2 and age by means of Kohonen's self-organizing maps (SOM).

Figure 14:
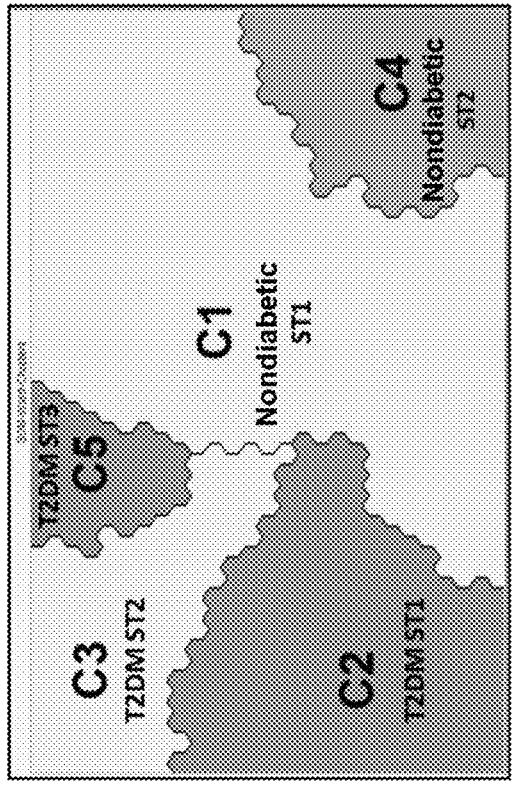
Figure 15:
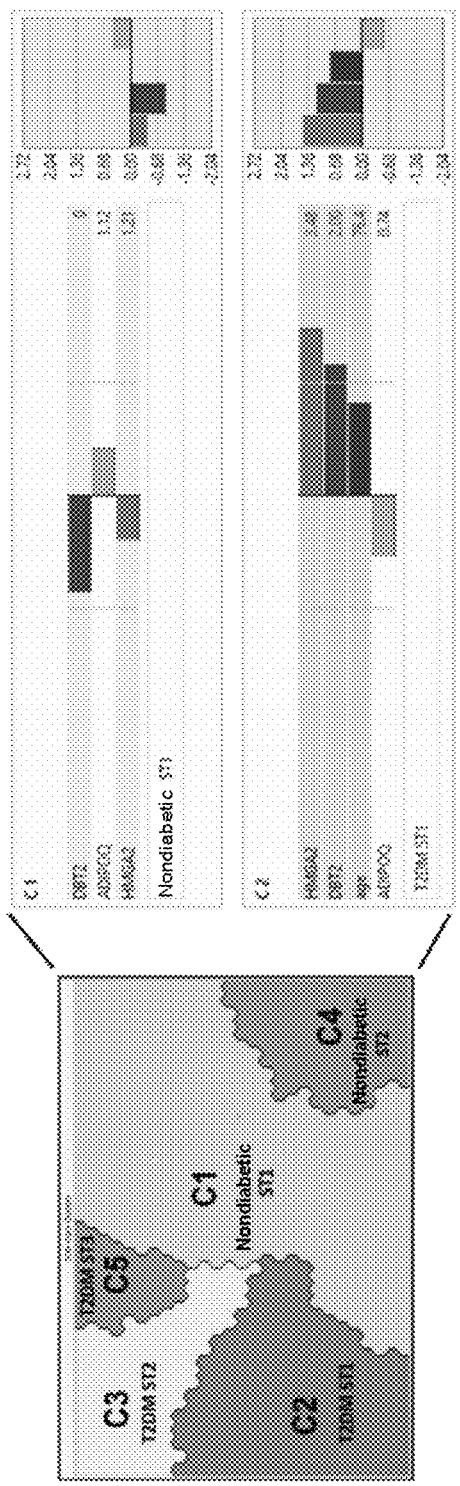
Figure 16:
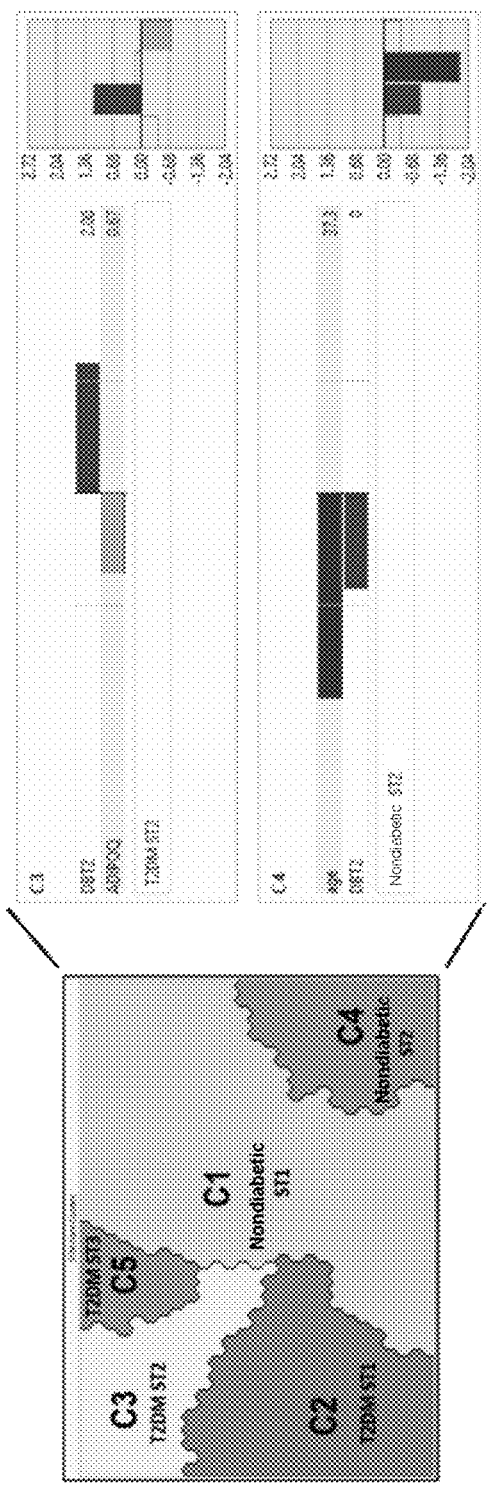
Figure 17:
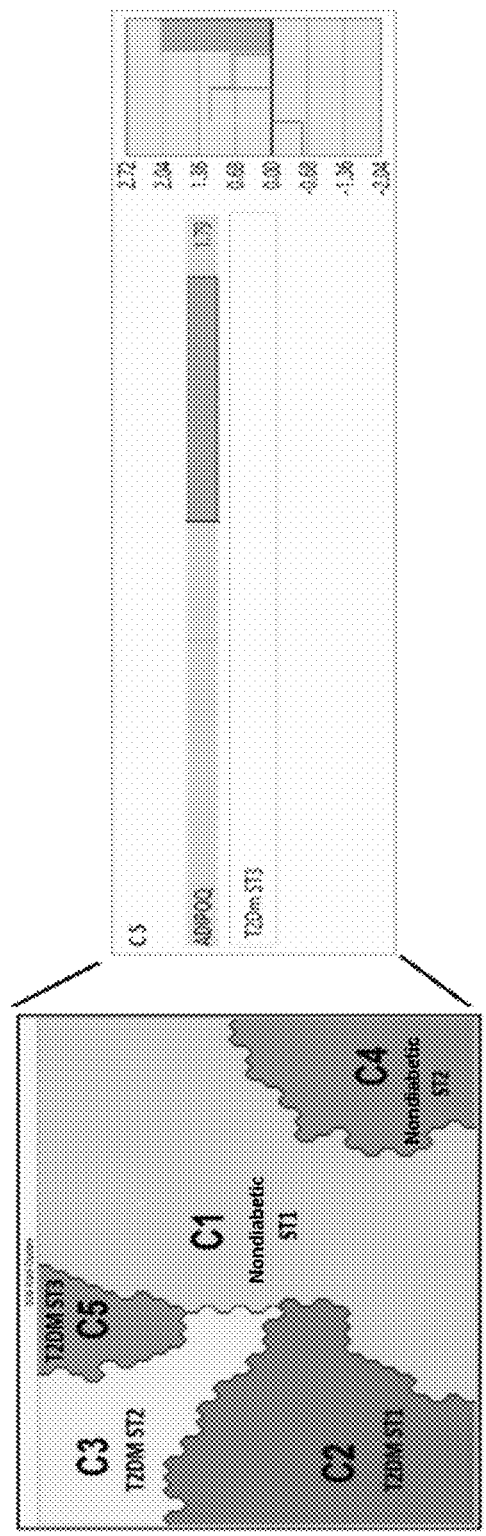

Surprisingly, FIG. 14 shows, after SOM analysis of the biomarkers ADIPOQ, HMGA2 and age (as further marker), a division of the patient population into five groups, and not into two groups, namely type 2 diabetics and nondiabetics, as would be expected following an HbA1c assay for example. The associated data are found in Table 2 and in FIGS. 15-17. The division of the patient population into five groups is also surprising in that patent specification DE10 2015 208 083 B3 disclosed a division of the patients into four groups, namely two overweight groups and two normal-weight groups.

The data analysis by means of self-organizing maps divides the subject population into five groups, taking the parameters HMGA2 expression and ADIPOQ expression into account. In this case, the nondiabetics are distributed into two clusters (C1 and C4). The average HMGA2 expression in both clusters is lowered compared to the average HMGA2 expression of the total population. The average ADIPOQ expression in cluster C1 is increased compared to the total population, and the expression in cluster C4 is, by contrast, lowered. The diabetics are subdivided into clusters C2, C3 and C5. The average HMGA2 expression is greatly increased in cluster C2, but the ADIPOQ expression is reduced. In cluster C3, the expression levels of both genes are lowered. The third diabetic cluster C5 has reduced HMGA2 expression; the ADIPOQ expression is greatly increased in this cluster.

ADIPOQ Segmentation

TABLE 2

| Cluster | Designation | Mean value, HMGA2 | Dev. [%] | HMGA2 | Mean value, ADIPOQ | Dev. [%] | ADIPOQ | Mean value, age |
|---|---|---|---|---|---|---|---|---|
| C1 | Nondiabetics ST1 | 1.21 | −27.2 | lowered | 1.12 | 17.4 | increased | 64.7 |
| C2 | T2D ST1 | 3.48 | 109.2 | greatly increased | 0.74 | −22.4 | lowered | 76.4 |
| C3 | T2D ST2 | 1.19 | −28.4 | lowered | 0.67 | −29.7 | lowered | 66.3 |
| C4 | Nondiabetics ST2 | 1.21 | −27.2 | lowered | 0.79 | −17.2 | lowered | 37.3 |
| C5 | T2D ST3 | 1.01 | −39.3 | lowered | 1.79 | 87.7 | greatly increased | 75.3 |

Without being tied to a theory, biological explanations for the clusters are as follows:

C2 (T2D subtype 1): dysfunctional adipose tissue owing to many preadipocytes (high HMGA2 value and comparatively low ADIPOQ value), more an "insulin-resistant" T2D subtype. Differentiation of the preadipocytes toward mature insulin-sensitive adipocytes would be desirable here, for example drugs from the group of the glitazones and metformin might be used here. However, there are indications that insulin and insulin-like growth factors promote the differentiation of preadipocytes in the direction of mature insulin-sensitive adipocytes (Ayoubi et al., 1999; Klemm et al., 2001). Therefore, it would also be conceivable to prescribe insulin and insulin production-promoting drugs in the case of high HMGA2 values.

C5 (T2D subtype 3): functional adipose tissue owing to many mature insulin-sensitive adipocytes (high ADIPOQ values), a generally "insulin-sensitive T2D subtype" can be expected. This T2D subtype presumably has a problem in insulin production/secretion in the β cells of the pancreas, and so a treatment here might aim at improving/increasing insulin production (e.g., sulfonylurea and glinides).

C3 (T2D subtype 2): dysfunctional adipose tissue presumably owing to impaired (but at least excessively low) adipokine production (average HMGA2 value (rather unremarkable) and very low ADIPOQ value), presumably more an "insulin-resistant" T2D subtype. Since there are presumably not too many preadipocytes here, the administration of metformin might help to increase the ADIPOQ values (see Kubota et al. 2006 and Adamia et al. 2007).

C1 (nondiabetics subtype 1): reflects functional adipose tissue with respect to adipose cell composition (preadipocyte-to-adipocyte ratio presumably in the "normal/healthy" range) and to function or adipokine production ("medium-high" ADIPOQ values).

C4 (nondiabetics subtype 2): reflects more a functional adipose tissue with respect to adipose cell composition (preadipocyte-to-adipocyte ratio presumably in the "normal/healthy" range). The lower ADIPOQ values compared to cluster C1 might possibly be associated with age (however, the reason might also be the relatively low number of subjects in cluster C4).

The invention claimed is:

1. A method for diagnosing a type II diabetes mellitus disease and treatment thereof in a human subject, comprising the steps of:
   a) puncturing the subcutaneous abdominal adipose tissue of the human subject to obtain a sample of adipose tissue from the human subject;
   b) extracting nucleic acid from the adipose tissue sample, wherein the nucleic acid is RNA;
   c) denaturing the RNA,
   d) reverse transcribing the denatured RNA into cDNA,
   e) pre-amplifying the cDNA, and
   f) measuring gene expression level of ADIPOQ gene via real-time polymerase chain reaction (PCR) using the pre-amplified cDNA obtained in step e);
   g) measuring gene expression level of a gene whose expression has linear/statistical correlation with that of the ADIPOQ gene via real-time PCR using the pre-amplified cDNA obtained in step e), wherein the gene whose expression has linear/statistical correlation with that of the ADIPOQ gene is HMGA2;
   h) obtaining a blood sample from the human subject and measuring one or more blood values of the human subject, wherein the one or more blood values are selected from the group consisting of total cholesterol, triglycerides, HbA1c, HDL cholesterol, non-HDL cholesterol, LDL cholesterol, CRP, blood sugar, fasting blood sugar and preprandial blood sugar and postprandial blood sugar;
   i) classifying the human subject into a risk group I, II, or III based on the gene expression levels of ADIPOQ and HMGA2 and the one or more blood values of the human subject and diagnosing the human subject with the type II diabetes mellitus disease; wherein the risk groups are:
   I) lowered relative gene expression level for ADIPOQ, greatly increased relative gene expression level for HMGA2 and at least one situation selected from the group consisting of increased HbA1c blood values relative to 5.7%, increased cholesterol values relative to 170 mg/dL for subjects <20 years old, 200 mg/dL for subjects between 20 and 30 years old, 220 mg/dL for subjects between 30 and 40 years old, 240 mg/dL for subjects >40 years old; increased triglycerides relative to 150 mg/dL; lowered HDL cholesterol relative to 40 mg/dL in men, 48 mg/dL in women; increased CRP relative to 5.0 mg/dL, increased fasting glucose relative to 100 mg/dL; increased preprandial glucose relative to 100 mg/dL; and increased postprandial glucose relative to 120 mg/dL;
   II) lowered gene expression level for ADIPOQ, lowered relative gene expression level for HMGA2, age >45, and at least one situation selected from the group consisting of increased HbA1c blood values relative to 5.7%, increased cholesterol values relative to 170 mg/dL for subjects for subjects >40 years old; increased triglycerides relative to 150 mg/dL; lowered HDL cholesterol relative to 40 mg/dL in men, 48 mg/dL in women; increased CRP relative to 5.0 mg/dL, increased fasting glucose relative to 100 mg/dL;

increased preprandial glucose relative to 100 mg/dL; and increased postprandial glucose relative to 120 mg/dL;

III) greatly increased relative gene expression level for ADIPOQ, lowered relative gene expression level for HMGA2 and at least one situation selected from the group consisting of increased HbA1c blood values relative to 5.7%, increased cholesterol values relative to 170 mg/dL for subjects <20 years old, 200 mg/dL for subjects between 20 and 30 years old, 220 mg/dL for subjects between 30 and 40 years old, 240 mg/dL for subjects >40 years old; increased triglycerides relative to 150 mg/dL; lowered HDL cholesterol relative to 40 mg/dL in men, 48 mg/dL in women; increased CRP relative to 5.0 mg/dL, increased fasting glucose relative to 100 mg/dL; increased preprandial glucose relative to 100 mg/dL; and increased postprandial glucose relative to 120 mg/dL;

wherein the relative gene expression levels for ADIPOQ and HMGA2 are:

lowered if the relative gene expression levels of ADIPOQ and HMGA2 deviate from a mean relative gene expression level of ADIPOQ and a mean relative gene expression level of HMGA2 by −10-50%;

greatly increased if the relative gene expression levels of ADIPOQ and HMGA2 deviate from a mean relative gene expression level of ADIPOQ and a mean relative gene expression level of HMGA2 by >50%;

wherein the mean relative gene expression level of ADIPOQ is 0.95365 and the mean relative gene expression level of HMGA2 is 1.663117;

wherein the one or more blood values are:

decreased if the one or more blood values deviate from the respective standard reference range by −10-50%;

increased if the one or more blood values deviate from the respective standard reference range by +10-50%;

j) treating the human subject diagnosed with the type II diabetes mellitus disease, comprising:
administering glitazones, metformin, or insulin if the human subject is classified into group I;
administering metformin if the human subject is classified into group II; or
administering sulfonylurea or glinides if the human subject is classified into group III.

2. The method as claimed in claim 1, wherein the sample of adipose tissue in step b) is ≤50 mg.

3. The method as claimed in claim 1, wherein treatment step j) comprises administering insulin to the human subject if the human subject is classified into group I during step i).

4. The method as claimed in claim 1, wherein treatment step j) comprises administering metformin to the human subject if the human subject is classified into group II during step i).

5. The method as claimed in claim 1, wherein treatment step j) comprises administering sulfonylurea to the human subject if the human subject is classified into group III during step i).

6. The method as claimed in claim 1, wherein treatment step j) comprises administering glinides to the human subject if the human subject is classified into group III during step i).

7. The method as claimed in claim 1, wherein treatment step j) comprises administering glitazones to the human subject if the human subject is classified into group I during step i).

8. The method as claimed in claim 1, wherein treatment step j) comprises administering metformin to the human subject if the human subject is classified into group I during step i).

* * * * *